(12) United States Patent
Cirpus et al.

(10) Patent No.: US 7,871,804 B2
(45) Date of Patent: Jan. 18, 2011

(54) METHOD FOR PRODUCING POLYUNSATURATED LONG-CHAIN FATTY ACIDS IN TRANSGENIC ORGANISMS

(75) Inventors: Petra Cirpus, Mannheim (DE); Jörg Bauer, Ludwigshafen (DE); Ernst Heinz, Hamburg (DE); Amine Abbadi, Ebergötzen (DE); Jelena Kirsch, Hamburg (DE)

(73) Assignee: BASF Plant Science GmbH, Ludwigshafen (DE)

( * ) Notice: Subject to any disclaimer, the term of this patent is extended or adjusted under 35 U.S.C. 154(b) by 510 days.

(21) Appl. No.: 11/793,854

(22) PCT Filed: Dec. 20, 2005

(86) PCT No.: PCT/EP2005/056957

§ 371 (c)(1),
(2), (4) Date: Aug. 8, 2007

(87) PCT Pub. No.: WO2006/069936

PCT Pub. Date: Jul. 6, 2006

(65) Prior Publication Data

US 2009/0094707 A1    Apr. 9, 2009

(30) Foreign Application Priority Data

Dec. 23, 2004    (DE) ................. 10 2004 062 294

(51) Int. Cl.
| C12N 9/10 | (2006.01) |
|---|---|
| C12N 15/00 | (2006.01) |
| C12N 1/20 | (2006.01) |
| C12P 21/06 | (2006.01) |
| C12P 19/34 | (2006.01) |
| C07H 21/04 | (2006.01) |
| C11B 1/00 | (2006.01) |
| A01H 9/00 | (2006.01) |

(52) U.S. Cl. ............... 435/193; 435/69.1; 435/91.1; 435/320.1; 435/252.3; 536/23.2; 554/8; 800/278; 800/291

(58) Field of Classification Search ............... 435/193, 435/69.1, 91.1, 320.1, 252.3; 536/23.2; 554/8; 800/278, 291
See application file for complete search history.

(56) References Cited

U.S. PATENT DOCUMENTS

| 2004/0034888 A1 | 2/2004 | Liu et al. |
|---|---|---|
| 2006/0168687 A1 | 7/2006 | Renz et al. |
| 2006/0174376 A1 | 8/2006 | Renz et al. |

FOREIGN PATENT DOCUMENTS

| FR | 2785911 A1 | 5/2000 |
|---|---|---|
| WO | WO-00/18889 A2 | 4/2000 |
| WO | WO-2004/076617 A2 | 9/2004 |
| WO | WO-2004/087902 A2 | 10/2004 |
| WO | WO 2004/087902 A2 * | 10/2004 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Kisselev L., Polypeptide release factors in prokaryotes and eukaryotes: same function, different structure. Structure, 2002, vol. 10: 8-9.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Seffernick et al., Melamine deaminase and Atrazine chlorohydrolase: 98 percent identical but functionally different. J. Bacteriol.,2001, vol. 183 (8): 2405-2410.*
Witkowski et al., Conversion of b-ketoacyl synthase to a Malonyl Decarboxylase by replacement of the active cysteine with glutamine. Biochemistry, 1999, vol. 38: 11643-11650.*
Chica et al., Semi-rational approaches to engineering enzyme activity: combining the benefits of directed evolution and rational design. Curr. Opi. Biotechnol., 2005, vol. 16: 378-384.*
Current Protocols in Molecular Biology, 1993, 2.10.1-2.10.16, Copyright 2000 by John Wiley & Sons, Inc.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*

(Continued)

*Primary Examiner*—Ganapathirama Raghu
(74) *Attorney, Agent, or Firm*—Connolly Bove Lodge & Hutz, LLP

(57) ABSTRACT

The invention relates to a method for producing polyunsaturated fatty acids in an organism, according to which nucleic acids coding for polypeptides with an acyl-CoA:lysophospholipid-acyltransferase activity are introduced into the organism. Advantageously, the nucleic acid sequences can be expressed in the transgenic organism optionally together with other nucleic acid sequences coding for polypeptides of the fatty acid or lipid metabolism. The invention also relates to the inventive nucleic acid sequences, nucleic acid constructs containing the inventive nucleic acid sequences, vectors containing the inventive nucleic acid sequences and/or the nucleic acid constructs, and transgenic organisms containing the nucleic acid sequences, nucleic acid constructs and/or vectors. The invention further relates to oils, lipids and/or fatty acids produced according to the inventive method, and to the use of the same.

20 Claims, 5 Drawing Sheets

OTHER PUBLICATIONS

Sauna et al., Silent polymorhisms speak: How they affect pharmacogenomics and the treatment of cancer. Cancer Res., 2007, vol. 67(20): 9609-9612.*

Sen et al., Developments in directed evolution for improving enzyme functions. Appl. Biochem. Biotechnol., 2007, vol. 143: 212-223.*

Domergue, F. et al., "Relief for fish stocks: oceanic fatty acids in transgenic oilseeds", Trends in Plant Science, 2005, vol. 10, No. 3, pp. 112-116.

"Lysophosphatidic acid acyltransferase, putative", UniProtKB Database Accession No. Q337H3, Jan. 24, 2006.

Yamashita, A. et al., "ATP-independent fatty acyl-coenzyme A synthesis from phospholipid", The Journal of Biological Chemistry, 2001, vol. 276, No. 29, pp. 26745-26752.

Dahlqvist, A. et al., "Phospholipid: diacylglycerol acyltransferase: an enzyme that catalyzes the acyl-CoA-independent formation of triacylglycerol in yeast and plants", PNAS, 2000, vol. 97, No. 12, pp. 6487-6492.

Yamashita, A. et al., "Acyltransferases and transacylases involved in fatty acid remodeling of phospholipids and metabolism of bioactive lipids in mammalian cells", J. Biochem., 1997, vol. 122, pp. 1-16.

\* cited by examiner

Fig. 1

Fig. 3, continued
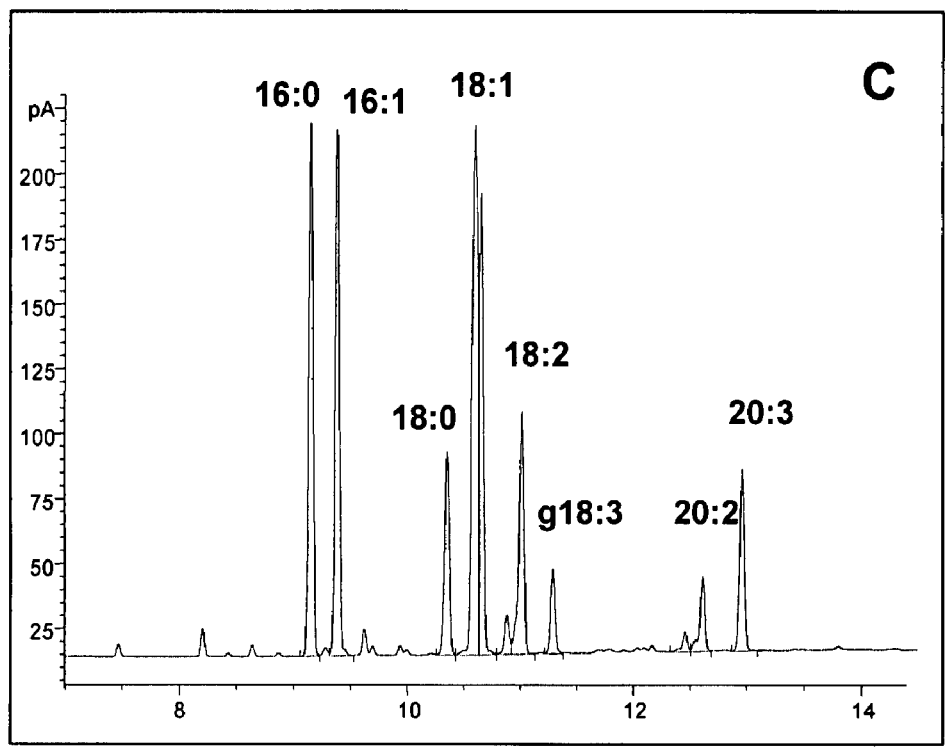

METHOD FOR PRODUCING POLYUNSATURATED LONG-CHAIN FATTY ACIDS IN TRANSGENIC ORGANISMS

RELATED APPLICATIONS

This application is a national stage application (under 35 U.S.C. 371) of PCT/EP2005/056957 filed Dec. 20, 2005, which claims benefit of German application 10 2004 062 294.9 filed Dec. 23, 2004.

Submission of Sequence Listing

The Sequence Listing associated with this application is filed in electronic format via EFS-Web and hereby incorporated by reference into the specification in its entirety. The name of the text file containing the Sequence Listing is Sequence_Listing_13477_00009. The size of the text file is 49 KB, and the text file was created on Apr. 6, 2010.

The present invention relates to a process for the production of polyunsaturated fatty acids in an organism by introducing, into the organism, nucleic acids which code polypeptides with acyl-CoA:lysophospholipid acyltransferase activity. These nucleic acid sequences, if appropriate together with further nucleic acid sequences which code for polypeptides of the fatty acid or lipid metabolism, can advantageously be expressed in the transgenic organism.

The invention furthermore relates to the nucleic acid sequences according to the invention, nucleic acid constructs comprising the nucleic acid sequences according to the invention, vectors comprising the nucleic acid sequences according to the invention and/or the nucleic acid constructs and transgenic organisms comprising the abovementioned nucleic acid sequences, nucleic acid constructs and/or vectors.

A further part of the invention relates to oils, lipids and/or fatty acids produced by the process according to the invention and to their use.

Fatty acids and triacylglycerides have a multiplicity of applications in the food industry, in animal nutrition, in cosmetics and in the pharmacological sector. Depending on whether they are free saturated or unsaturated fatty acids or else triglycerides with an elevated content of saturated or unsaturated fatty acids, they are suitable for very different applications; thus, polyunsaturated fatty acids, for example, are added to baby formula to improve the nutritional value. Polyunsaturated ω3-fatty acids and ω6-fatty acids are therefore an important constituent in animal and human nutrition. Owing to the present-day composition of human food, an addition of polyunsaturated ω3-fatty acids, which are mainly found in fish oils, to the food is particularly important. Thus, for example, polyunsaturated ω3-fatty acids such as docosahexaenoic acid (=DHA, $C22:6^{\Delta 4,7,10,13,16,19}$) or eicosapentaenoic acid (=EPA, $C20:5^{\Delta 5,8,11,14,17}$) are added to baby formula to improve the nutritional value. The unsaturated fatty acid DHA is said to have a positive effect on the development of the brain.

The polyunsaturated ω3-fatty acids are said to have a positive effect on the cholesterol level in the blood and thus on the possibility of preventing heart disease. The risk of heart disease, stroke or hypertension can be reduced markedly by adding these ω3-fatty acids to the food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Hereinbelow, polyunsaturated fatty acids are referred to as PUFA, PUFAs, LCPUFA or LCPUFAs (poly unsaturated fatty acid=PUFA, long chain holy unsaturated fatty acid=LCPUFA).

The various fatty acids and triglycerides are mainly obtained from microorganisms such as *Mortierella* and *Schizochytrium* or from oil-producing plants such as soybean or oilseed rape, algae such as *Crypthecodinium* or *Phaeodactylum*, where they are obtained, as a rule, in the form of their triacylglycerides (=triglycerides=triglycerols). However, they can also be obtained from animals, such as, for example, fish. The free fatty acids are advantageously prepared by hydrolysis. Higher polyunsaturated fatty acids such as DHA, EPA, arachidonic acid (=ARA, $C20:4^{\Delta 5,8,11,14}$), dihomo-γ-linolenic acid ($C20:3^{\Delta 8,11,14}$) or docosapentaenoic acid (DPA, $C22:5^{\Delta 7,10,13,16,19}$) cannot be isolated from oil crops such as oilseed rape, soybean, sunflower or safflower. Conventional natural sources of these fatty acids are fish such as herring, salmon, sardine, redfish, eel, carp, trout, halibut, mackerel, zander or tuna, and algae.

Owing to the positive characteristics of the polyunsaturated fatty acids, there has been no lack of attempts in the past to make available genes which are involved in the synthesis of fatty acids or triglycerides for the production of oils in various organisms with a modified content of unsaturated fatty acids. Thus, WO 91/13972 and its US equivalent describes a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, WO 96/21022, WO 00/21557 and WO 99/27111, while the application for the production of fatty acids in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microorganisms such as *Thraustochytrium* strains or *Schizochytrium* strains, algae such as *Phaeodactylum tricornutum* or *Crypthecodinium* species, ciliates such as *Stylonychia* or *Colpidium*, fingi such as *Mortierella, Entomophthora* or *Mucor*. Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible. However, only limited amounts of the desired polyunsaturated fatty acids such as DPA, EPA or ARA can be produced with the aid of the abovementioned microorganisms, and, depending on the microorganism used, these are generally obtained as fatty acid mixtures of, for example, EPA, DPA and DHA.

Alternatively, the production of fine chemicals on the large scale can advantageously be effected in plants, which are developed in such a way that they produce the abovementioned PUFAs. Plants which are particularly suitable for this purpose are oil crops which contain large amounts of lipid compounds, such as oilseed rape, canola, linseed, soybeans, sunflowers, borage and evening primrose. However, other useful plants, which contain oils or lipids and fatty acids are also suitable, as mentioned in the detailed description of the present invention. A series of mutant plants which produce a spectrum of desirable lipids and fatty acids, cofactors and enzymes has been developed by means of conventional breeding. However, the selection of novel plant varieties with an improved production of a certain molecule is a time-consuming and difficult procedure or indeed impossible if the compound does not naturally occur in the plant in question, as in the case of polyunsaturated $C_{18}$-, $C_{20}$- and $C_{22}$-fatty acids and fatty acids with longer carbon chains.

There has therefore not been a lack of attempts in the past to make available genes which are involved in fatty acid or triglyceride synthesis for the production of oils in various plants with a modified content of polyunsaturated fatty acids. However, it has not been possible to date to produce longer-chain polyunsaturated $C_{20}$- and/or $C_{22}$-fatty acids such as EPA or ARA in plants.

However, the gene-technological modifications of the fatty acid metabolic pathway via the introduction and expression of, for example, desaturases also leads to only relatively minor increases in the productivity in other organisms such as micro-organisms such as algae or fungi. One reason may be the highly complex fatty acid metabolism. Thus, the incorporation of polyunsaturated fatty acids into membrane lipids and/or into triacylglycerides and their degradation and interconversion is highly complex and is as yet not fully elucidated and understood in biochemical and, specifically, genetic terms.

The biosynthesis of LCPUFAs and the incorporation of LCPUFAs into membranes or triacylglycerides takes place via various metabolic pathways (Abbadi et al. (2001) European Journal of Lipid Science & Technology 103:106-113). In bacteria such as *Vibrio* and microalgae such as *Schizochytrium*, malonyl-CoA is converted via an LCPUFA-producing polyketide synthase into LCPUFAs (Metz et al. (2001) Science 293: 290-293; WO 00/42195; WO 98/27203; WO 98/55625). In microalgae such as *Phaeodactylum* and mosses such as *Physcomitrella*, unsaturated fatty acids such as linoleic acid or linolenic acid are, in the form of their acyl-CoAs, converted into LCPUFAs in a plurality of desaturation and elongation steps (Zank et al. (2000) Biochemical Society Transactions 28: 654-658). In mammals, the biosynthesis of DHA comprises, in addition to desaturation and elongation steps, a reduction in chain length via β-oxidation.

In microorganisms and lower plants, LCPUFAs are present either exclusively in the form of membrane lipids, as is the case in *Physcomitrella* and *Phaeodactylum*, or else they are present both in membrane lipids and in triacylglycerides, as is the case in *Schizochytrium* and *Mortierella*. The incorporation of LCPUFAs into lipids and oils is catalyzed by a variety of acyltransferases and transacylases, which are already known for the incoporation of saturated and unsaturated fatty acids (Slabas (2001) J. Plant Physiology 158: 505-513; Frentzen (1998) Fett/Lipid 100: 161-166; Cases et al. (1998) Proc. Nat. Acad. Sci. USA 95: 13018-13023). The acyltransferases are enzymes of what is known as the Kennedy pathway; they are localized on the cytoplasmatic side of the membrane system of the endoplasmic reticulum, herein-below referred to as the "ER". In experiments, ER membranes can be isolated from various organisms as what are known as "microsomal fractions" (Knutzon et al. (1995) Plant Physiology 109: 999-1006; Mishra & Kamisaka (2001) Biochemistry 355: 315-322; U.S. Pat. No. 5,968,791). These ER-bound acyltransferases in the microsomal fraction utilize acyl-CoA as the activated form of the fatty acids. Glycerol-3-phosphate acyltransferase, hereinbelow referred to as GPAT, catalyzes the incorporation of acyl groups at the sn-1 position of glycerol-3-phosphate. 1-Acylglycerol-3-phosphate acyltransferase (E.C. 2.3.1.51), also referred to as lysophosphatidic acid acyltransferase, hereinbelow referred to as LPAAT, catalyses the incorporation of acyl groups at the sn-2 position of lysophosphatidic acid, hereinbelow abbreviated to LPA. Following dephosphorylation of phosphatidic acid by phosphatidic acid phosphatase, diacylglycerol acyltransferase, hereinbelow referred to as DAGAT, catalyzes the incorporation of acyl groups at the sn-3 position of diacylglyerol. Besides these enzymes of the Kennedy pathway, further enzymes are involved in the incorporation of fatty acids into triacylglycerides, which enzymes are capable of incorporating acyl groups from membrane lipids into triacylglycerides, such as phospholipid diacylglycerol acyltransferase, hereinbelow referred to as PDAT, and lysophosphatidylcholine acyltransferase, hereinbelow referred to as LPCAT.

The enzymatic activity of an LPCAT has first been described in rats (Land (1960) J. Biol. Chem. 235: 2233-2237). In plants, there exists a plastidial isoform of LPCAT (Akermoun et al. (2000) Biochemical Society Transactions 28: 713-715) and an ER-bound isoform (Tumaney and Rajasekharan (1999) Biochimica et Biophysica Acta 1439: 47-56; Fraser and Stobart, Biochemical Society Transactions (2000) 28: 715-7718). LPCATs are involved in the biosynthesis and the transacylation of polyunsaturated fatty acids, both in animals and in plants (Stymne and Stobart (1984) Biochem. J. 223: 305-314; Stymne and Stobart (1987) in 'The Biochemistry of Plants: a Comprehensive Treatise', Vol. 9 (Stumpf, P. K. ed.) pp. 175-214, Academic Press, New York). An important function of LPCAT or, in more general terms, of an acyl-CoA:lysophospholipid acyltransferase, hereinbelow referred to as LPLAT, in the ATP-independent synthesis of acyl-CoA from phospholipids has been described by Yamashita et al. (2001) J. Biol. Chem. 276: 26745-26752.

Higher plants contain polyunsaturated fatty acids such as linoleic acid (C18:2) and, linolenic acid (C18:3). Aarachidonic acid (ARA), eicosapentaenoic acid (EPA) and docoahexaenoic acid (DHA) however, are not found at all in the seed oil of higher plants, or only in miniscule amounts (E. Ucciani: Nouveau Dictionnaire des Huiles Vegetales [New Dictionary of Vegetable Oils]. Technique & Documentation—Lavoisier, 1995. ISBN: 2-7430-0009-0). The production of LCPUFAs in higher plants, preferably in oil crops such as oilseed rape, linseed, sunflower and soybean, would be advantageous since large amounts of high-quality LCPUFAs for the food industry, animal nutrition and pharmaceutical purposes might be obtained economically. To this end, it is advantageous to introduce, into oil crops, genes which code enzymes of the LCPUFA biosynthesis via recombinant methods and to express them therein. These genes code for example for a Δ6-desaturase, Δ6-elongase, Δ5-desaturase, Δ5-elongase and Δ4-desaturase. These genes can advantageously be isolated from microorganisms, animals and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans*.

The first transgenic plants which contain and express genes encoding LCPUFA biosynthesis enzymes and which produce LCPUFAs were described for the first time in DE 102 19 203 (process for the production of polyunsaturated fatty acids in plants). However, these plants produce LCPUFAs in amounts which require further optimization for processing the oils which are present in the plants.

To make possible the fortification of food and of feed with these polyunsaturated fatty acids, there is therefore a great need for a simple, inexpensive process for the production of these polyunsaturated fatty acids, specifically in eukaryotic systems.

It was therefore an object to develop a process for the production of polyunsaturated fatty acids in a eukaryotic organism. This object was achieved by the process according to the invention for the production of polyunsaturated fatty acids in an organism, which comprises the following steps:

a) introducing, into the organism, at least one nucleic acid sequence selected from the group consisting of:
   i) nucleic acid sequences with the sequence shown in SEQ ID NO: 1, SEQ ID NO: 3 or SEQ ID NO: 5, which code for a polypeptide with an acyl-CoA:lysophospholipid acyltransferase activity; or
   ii) nucleic acid sequences which, as the result of the degeneracy of the genetic code, can be derived from the sequence shown in SEQ ID NO: 1, SEQ ID NO: 3 or SEQ ID NO: 5; or
   iii) derivatives of the nucleic acid sequence shown in SEQ ID NO: 1, SEQ ID NO: 3 or SEQ ID NO: 5, which code for polypeptides with the amino acid sequence shown in SEQ ID NO: 2, SEQ ID NO: 4 or SEQ ID NO: 6 and which have at least 40% homology with SEQ ID NO: 2, SEQ ID NO: 4 or SEQ ID NO: 6 at the amino acid level and have an equivalent acyl-CoA:lysophospholipid acyltransferase activity, and b) culturing and harvesting the organism.

The polyunsaturated fatty acids produced in the process according to the invention advantageously comprise at least two, advantageously three, double bonds. The fatty acids especially advantageously comprise four or five double bonds. Fatty acids produced in the process advantageously have 16, 18, 20 or 22 C atoms in the fatty acid chain. These fatty acids can be produced in the process as a single product or be present in a fatty acid mixture.

The nucleic acid sequences used in the process according to the invention are isolated nucleic acid sequences which code for polypeptides with acyl-CoA:lysophospholipid acyltransferase activity.

The polyunsaturated fatty acids produced in the process are advantageously bound in membrane lipids and/or triacylglycerides, but may also be present in the organisms as free fatty acids or else bound in the form of other fatty acid esters. Here, they can be present, as has been said above, as "pure products" or else advantageously in the form of mixtures of various fatty acids or mixtures of different glycerides. Here, the various fatty acids bound in the triacylglycerides can be derived from short-chain fatty acids having 4 to 6 C atoms, medium-length-chain fatty acids with 8 to 12 C atoms or long-chain fatty acids with 14 to 24 C atoms, with long-chain fatty acids being preferred; especially preferred are the long-chain $C_{18}$-, $C_{20}$- and/or $C_{22}$-fatty acids (LCPUFAs).

The process according to the invention advantageously yields fatty acid esters with polyunsaturated $C_{16}$-, $C_{19}$-, $C_{20}$- and/or $C_{22}$-fatty acid molecules with at least two double bonds in the fatty acid ester. These fatty acid molecules preferably comprise three, four or five double bonds and advantageously lead to the synthesis of hexadecadienoic acid (16: $2^{\Delta 9,12}$), γ-linolenic acid (=GLA, $C18:3^{\Delta 6,9,12}$), stearidonic acid (=SDA, $C18:4^{\Delta 6,9,12,15}$), dihomo-γ-linolenic acid (=DGLA, $20:3^{\Delta 8,11,14}$), eicosatetraenoic acid (=ETA, $C20:4^{\Delta 5,8,11,14}$), arachidonic acid (ARA), eicosapentaenoic acid (EPA), or mixtures of these, preferably to the synthesis of EPA and/or ARA.

The fatty acid esters with polyunsaturated $C_{16}$-, $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidyl-choline, phosphatidylserine, phosphatidylglycerol, phosphatidylinositol or diphosphatidylglycerol, monoacylglycerides, diacylglycerides, triacylglycerides or other fatty acid esters such as the acetylcoenzyme A esters which comprise the polyunsaturated fatty acids with at least two, preferably three double bonds, from the organisms which have been used for the preparation of the fatty acid esters. In addition to these esters, the polyunsaturated fatty acids are also present in the organisms, advantageously the plants as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, preferably in a transgenic plant. Since a plurality of reaction steps are performed by the compounds exadecadienoic acid (C16:2), linoleic acid (C18: 2) and linolenic acid (C18:3) in the process according to the invention, the end products of the process such as, for example, arachidonic acid (ARA) or eicosapentaenoic acid (EPA) are not obtained as absolutely pure products; minor traces of the precursors are always present in the end product. If, for example, both linoleic acid and linolenic acid are present in the starting organism and the starting plant, the end products such as ARA and EPA are present as mixtures. The precursors should advantageously not amount to more than 20% by weight, preferably not to more than 15% by weight, especially preferably not to more than 10% by weight, most preferably not to more than 5, 4, 3, 2, 10% by weight, based on the amount of the end product in question. Advantageously, only ARA or only EPA bound or as free fatty acids, are produced as end products in a transgenic plant in the process according to the invention. If compounds (ARA+EPA) are produced simultaneously, they are advantageously produced in a ratio of at least 1:2 (EPA:ARA), advantageously of at least 1:3, preferably of at least 1:4, especially preferably of at least 1:5.

Chemically pure polyunsaturated fatty acids or fatty acid compositions can also be synthesized by the above described process. To this end, the fatty acids or fatty acid compositions are isolated from the organism such as the microorganisms or the plants or the culture medium in the known manner, for example via extraction, distillation, crystallization, chromatography or combinations of these methods. These chemically pure polyunsaturated fatty acids or fatty acid compositions are advantageous for applications in the field of the food industry, the cosmetics industry and, in particular, the pharmaceuticals industry.

In principle, all organisms such as fungi, such as *Mortierella* or *Thraustochytrium*, yeasts such as *Saccharomyces* or *Schizosaccharomyces*, mosses such as *Physcomitrella* or *Ceratodon*, nonhuman animals such as *Caenorhabditis*, algae such as *Crypthecodinium* or *Phaeodactylum* or plants such as dicotyledonous or monocotyledonous plants are suitable as organism for the production in the process according to the invention. Organisms which are advantageously used in the process according to the invention are organisms which belong to the oil-producing organisms, that is to say which are used for the production of oils, such as fungi, such as *Mortierella* or *Thraustochytrium*, algae such as *Crypthecodinium* or *Phaeodactylum*, or plants, in particular oil crop plants which contain large amounts of lipid compounds, such as peanut, oilseed rape, canola, sunflower, safflower, poppy, mustard, hemp, castor-oil plant, olive, sesame, *Calendula, Punica,* evening primrose, *verbascum*, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassaya, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica,* evening primrose, pumpkin/squash, linseed, soybean, borage, trees (oil palm, coconut). Especially preferred are plants which are high in C18:2- and/or C18:3-fatty acids, such as sunflower, safflower, tobacco, *verbascum*, sesame, cotton, pumpkin/squash, poppy, evening primrose, walnut, linseed, hemp or thistle. Most preferred plants are plants such as safflower, sunflower, poppy, evening primrose, walnut, linseed or hemp.

It is advantageous for the above-described process according to the invention additionally to introduce, into the organism, further nucleic acids which code enzymes of the fatty acid or lipid metabolism, in addition to the nucleic acids introduced in process step (a).

In principle, all genes of the fatty acid or lipid metabolism can be used in the process for the production of polyunsaturated fatty acids, advantageously in combination with the inventive acyl-CoA:lysophospholipid acyltransferase. Genes of the fatty acid or lipid metabolism selected from the group consisting of acyl-CoA dehydrogenase(s), acyl-ACP [=acyl carrier protein] desaturase(s), acyl-ACP thioesterase(s), fatty acid acyl transferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously used in combination with acyl-CoA:lysophospholipid acyltransferase. Genes selected from the group of the Δ4-desaturases, Δ5-desaturases, Δ6-desaturases, Δ8-desaturases, Δ9-desaturases, Δ12-desaturases, Δ5-elongases, Δ6-elongases or Δ9-elongases are especially preferably used in combination with the inventive acyl-CoA:lysophospholipid acyltransferase in the process according to the invention.

Owing to the enzymatic activity of the nucleic acids used in the process according to the invention which code polypeptides with acyl-CoA:lysophospholipid acyltransferase activity, advantageously in combination with nucleic acid sequences which code polypeptides of the fatty acid or lipid metabolism, with Δ4-, Δ5-, Δ6-, Δ8-desaturase or Δ5-, Δ6- or Δ9-elongase activity, a wide range of polyunsaturated fatty acids can be produced in the process according to the invention. Depending on the choice of the organisms, such as the advantageous plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta9,12}$) is present as unsaturated fatty acid in the plant used for the process, the process can only afford GLA, DGLA and ARA as products, all of which can be present as free fatty acids or in bound form. If only α-linolenic acid (=ALA, $C18:3^{\Delta9,12,15}$) is present as unsaturated fatty acid in the plant used for the process, as is the case, for example, in linseed, the process can only afford SDA, ETA and EPA as products, all of which can be present as free fatty acids or in bound form, as described above. Owing to the modification of the activity of the enzyme acyl-CoA:lysophospholipid acyltransferase advantageously in combination with Δ5- and Δ6-desaturase and Δ6-elongase, or Δ5-, Δ8-desaturase, and Δ9-elongase, or in combination with only the first two genes of the synthetic chain, Δ6-desaturase and Δ6-elongase, or Δ8-desaturase and Δ9-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase is additionally introduced into the organisms, advantageously into the plant, ARA or EPA are additionally formed. This also applies to organisms into which the Δ8-desaturase and Δ9-elongase had previously been introduced.

To increase the yield in the above-described process for the production of oils and/or triglycerides with an advantageously elevated content of polyunsaturated fatty acids, it is advantageous to increase the amount of starting material for the synthesis of fatty acids; this can be achieved for example by introducing, into the organism, a nucleic acid which codes a polypeptide with Δ12-desaturase activity. This is particularly advantageous in oil-producing organisms such as oilseed rape which is high in oleic acid. Since these organisms are only low in linoleic acid (Mikoklajczak et al., Journal of the American Oil Chemical Society, 38, 1961, 678-681), the use of a Δ12-desaturase for producing the starting material linoleic acid is advantageous.

Nucleic acids used in the process according to the invention are advantageously derived from plants such as algae such as *Isochrysis* or *Crypthecodinium*, algae/diatoms such as *Phaeodactylum*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, yeasts or animals such as nematodes such as *Caenorhabditis*, insects or humans. The nucleic acids are advantageously derived from fungi, animals, or from plants such as algae or mosses, preferably from nematodes such as *Caenorhabditis*.

The process according to the invention advantageously employs the above-mentioned nucleic acid sequences or their derivatives or homologues which code polypeptides which retain the enzymatic activity of the proteins coded by wild-type nucleic acid sequences. These sequences, individually or in combination with the nucleic acid sequences which code for acyl-CoA:lysophospholipid acyltransferase, are cloned into expression constructs and used for the introduction into, and expression in, organisms. These expression constructs make possible an optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with the nucleic acid sequence according to the invention which codes for the acyl-CoA:lysophospholipid acyltransferase, a gene construct or a vector as described above, alone or in combination with further nucleic acid sequences which code proteins of the fatty acid or lipid metabolism. In a further preferred embodiment, this process furthermore comprises the step of obtaining the fine chemical from the culture. The culture can, for example, take the form of a fermentation culture, for example in the case of the cultivation of microorganisms, such as, for example, *Mortierella, Saccharomyces* or *Thraustochytrium*, or a greenhouse- or field-grown culture of a plant. The cell or the organism produced thus is advantageously a cell of an oil-producing organism, such as an oil crop, such as, for example, peanut, oilseed rape, canola, linseed, hemp, peanut, soybean, safflower, hemp, sunflowers or borage.

In the case of plant cells, plant tissue or plant organs, "growing" is understood as meaning, for example, the cultivation on or in a nutrient medium, or in the case of the intact plant on or in a substrate, for example in a hydroponic culture, potting compost or on arable land.

For the purposes of the invention, "transgenic" or "recombinant" means with regard to, for example, a nucleic acid sequence, an expression cassette (=gene construct) or a vector comprising the inventive nucleic acid sequence or an organism transformed with the nucleic acid sequences, expression cassettes or vectors according to the invention, all those constructions brought about by recombinant methods in which either a) the nucleic acid sequence according to the invention, or
b) a genetic control sequence which is operatively linked with the nucleic acid sequence according to the invention, for example a promoter, or
c) a) and b)

are not located in their natural genetic environment or have been modified by recombinant methods, it being possible for the modification to take the form of, for example, a substitution, addition, deletion, inversion or insertion of one or more nucleotide residues.

The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequence according to the invention with the corresponding acyl-CoA:lysophospholipid acyltransferase gene becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic organism or transgenic plant for the purposes of the invention is therefore understood as meaning, as above, that the nucleic acids used in the process are not at their natural locus in the genome of an organism, it being possible for the nucleic acids to be expressed homologously or heterologously. However, as mentioned, transgenic also means that, while the nucleic acids according to the invention are at their natural position in the genome of an organism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierella* or plants such as oil crops.

Organisms or host organisms suitable for the nucleic acids, the expression cassettes or the vectors used in the process according to the invention are, in principle, advantageously all organisms which are capable of synthesizing fatty acids, specifically unsaturated fatty acids, and/or which are suitable for the expression of recombinant genes. Examples which may be mentioned are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Saprolegnia*, or *Pythium*, bacteria, such as the genus *Escherichia*, yeasts, such as the genus *Saccharomyces*, cyanobacteria, ciliates, algae or protozoans such as dinoflagellates, such as *Crypthecodinium*. Preferred organisms are those which are naturally capable of synthesizing substantial amounts of oil, such as fungi, such as *Mortierella alpina, Pythium insidiosum*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula, Mortierella* or *Saccharomyces cerevisiae* being especially preferred. In principle, host organisms are, in addition to the abovementioned transgenic organisms, also transgenic animals, advantageously nonhuman animals, for example *C elegans*.

Further utilizable host cells are detailed in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

Transgenic plants which contain the polyunsaturated fatty acids synthesized in the process according to the invention can advantageously be marketed directly without there being any need for the oils, lipids or fatty acids synthesized to be isolated. Plants in the process according to the invention are understood as meaning intact plants and all plant tissue, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat during pressing. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using fuller's earth or active charcoal. At the end, the product is deodorized, for example using steam.

The PUFAs or LCPUFAs produced by this process are advantageously $C_{18}$-, $D_{20}$- or $C_{22}$-fatty acid molecules, with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the above-described process, especially preferably oils, lipids or a fatty acid composition comprising PUFAs and being derived from transgenic plants.

A further embodiment according to the invention is the use of the oil, lipid, the fatty acids and/or the fatty acid composition in feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The amount of unsaturated esterified fatty acids preferably amounts to approximately 30%, a content of 50% is especially preferred, a content of 60%, 70%, 80% or more is most preferred. The fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, for example, sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least two double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operatively with a functional expression unit which comprises at least one sequence which ensures the expression of a gene and at least one sequence which ensures the polyadenylation of a functionally transcribed gene. The nucleic acids are advantageously introduced into the organisms via multi-expression cassettes or constructs for multi-parallel expression, advantageously into the plants for the multi-parallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms, which are related to algae and a few fungi also accumulate substantial amounts of PUFAs in the triacylglycerol fraction. This is why nucleic acid molecules which are isolated from such strains which also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates which are advantageously used for the inventive acyl-CoA:lysophospholipid acyltransferases are $C_{16}$-, $C_{18}$-, $C_{20}$- or $C_{22}$-fatty acids.

To produce the long-chain PUFAs according to the invention, the polyunsaturated $C_{16}$- or $C_{18}$-fatty acids must first be desaturated by the enzymatic activity of a desaturase and subsequently be elongated by at least two carbon atoms via an elongase. After one elongation cycle, this enzyme activity gives $C_{18}$- or $C_{20}$-fatty acids and after two or three elongation cycles $C_{22}$- or $C_{24}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four or five double bonds, especially preferably to give $C_{20}$- and/or $C_{22}$-fatty acids with at least two double bonds in the fatty acid molecule, preferably with three, four or five double bonds in the molecule. After a first desaturation and the elongation have taken place, further desaturation steps such as, for example, such a desaturation in the Δ5-position may take place. Products of the process according to the invention, which are especially preferred are dihomo-γ-linolenic acid, arachidonic acid, eicosapentaenoic acid, docosapentaenoic acid and/or docosahexaenoic acid. The $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of the fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

Owing to the use of the nucleic acids according to the invention which code for acyl-CoA:lysophospholipid acyltransferases, the amount of polyunsaturated fatty acids produced in the process can be increased by at least 10%, preferably by at least 15%, especially preferably by at least 20%, very especially preferably by at least 50% and most preferably by at least 100% in comparison with the wild type of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms such as yeasts such as *Saccharomyces* or *Schizosaccharomyces*, fungi such as *Mortierella, Aspergillus, Phytophtora, Entomophthora, Mucor* or *Traustochytrium*, algae such as *Isochrysis, Phaeodactylum* or *Crypthecodinium* are used as organisms in the process according to the invention, they are grown or cultured, advantageously by fermentation, in the manner with which the skilled worker is familiar.

As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while passing in oxygen. The pH of the liquid medium can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semi-batchwise or continuously. An overview over known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphate or sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The culture is continued until formation of the desired product is at a maximum. This aim is normally achieved within 10 to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The terms production or productivity are known in the art and comprise the concentration of the fermentation product (compounds of the formula I) which is formed within a certain period of time and in a certain fermentation volume (for example kg product per hour per liter). The term production efficiency comprises the period of time which is required for obtaining a certain production quantity (for example the time required by the cell for establishing a certain throughput rate of a fine chemical). The term yield or product/carbon yield is known in the art and comprises the efficiency of the conversion of the carbon source into the product (i.e. the fine chemical). This is usually expressed for example as kg product per kg carbon source. By increasing the yield or production of the compound, the amount of the molecules obtained of this compound in a certain culture quantity is increased over a predetermined period of time. The terms biosynthesis or biosynthetic pathway are known in the art and comprise the synthesis of a compound, preferably an organic compound, by a cell starting from intermediates, for example in a multistep, highly regulated process. The terms catabolism or catabolic pathway are known in the art and comprise the cleavage of a compound, preferably of an organic compound, by a cell into catabolites (in more general terms, smaller or less complex molecules), for example in a multistep, highly regulated process. The term metabolism is known in the art and comprises the totality of the biochemical reactions which take place in an organism. The metabolism of a certain compound (for example the metabolism of a fatty acid) will then comprise the totality of the biosynthetic, modifying and catabolic pathways of this compound in the cell which concern this compound.

The fatty acids obtained in the process are also suitable as starting material for the chemical synthesis of further products of interest. For example, they can be used in combination with one another or alone for the preparation of pharmaceuticals, foodstuffs, animal feeds or cosmetics.

The invention furthermore relates to isolated nucleic acid sequences coding for polypeptides with acyl-CoA:lysophospholipid acyltransferase activity which specifically convert $C_{16}$-, $C_{18}$-, $C_{20}$- and $C_{22}$-fatty acids with at least one double bond in the fatty acid molecule, where the nucleic acid sequences are sequences selected from the group consisting of:
  a) nucleic acid sequences with the sequence shown in SEQ ID NO: 1, SEQ ID NO: 3 or SEQ ID NO: 5,
  b) nucleic acid sequences which, as the result of the degeneracy of the genetic code, can be derived from the coding sequence shown in SEQ ID NO: 1, SEQ ID NO: 3 or SEQ ID NO: 5,
  c) derivatives of the nucleic acid sequence shown in SEQ ID NO: 1, SEQ ID NO: 3 or SEQ ID NO: 5, which code for polypetides with the amino acid sequence shown in SEQ ID NO: 2, SEQ ID NO: 4 or SEQ ID NO: 6 and which have at least 40% homology at the amino acid level with SEQ ID NO: 2, SEQ ID NO: 4 or SEQ ID NO: 6 and which have an acyl-CoA:lysophospholipid acyltransferase activity.

The abovementioned nucleic acid sequences are advantageously derived from a eukaryotic organism, especially preferably from *Ostreococcus tauri* or *Mantoniella squamata*.

The nucleic acid sequences used in the process which code for proteins with acyl-CoA:lysophospholipid acyltransferase activity or for proteins of the fatty acid or lipid metabolism are advantageously introduced in an expression cassette (=nucleic acid construct) which makes possible the expression of the nucleic acids in an organism, advantageously a plant or a microorganism.

To introduce the nucleic acids used in the process, the nucleic acids used in the process are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step. Suitable cloning vectors are generally known to the skilled worker. These include, in particular, vectors which are capable of replication in microbial systems, that is to say mainly vectors which ensure efficient cloning in yeasts or fungi and which, at the same time, make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the Agro-bacterium-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E Coli* and in *Agrobacterium*. These binary vectors include vectors from the series pBIB-HYG, pPZP, pBecks, pGreen. In accordance with the invention, pBin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared in a similar manner, using ligase. In this context, a particular nucleic acid construct, or vector or plasmid construct, can have one or else more than one codogenic gene segment. The codogenic gene segments in these constructs are preferably linked operatively with regulatory sequences. The regulatory sequences include, in particular, plant sequences such as the above-described promoters and terminator sequences. The constructs can advantageously be stably propagated in microorganisms, in particular in *Escherichia coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient PUFA producers.

There exists a series of mechanisms by which the modification of an acyl-CoA:lysophospholipid acyltransferase protein according to the invention can directly influence the yield, production and/or production efficiency of a fine chemical in an oil crop plant or in a microorganism. The number or activity of the acyl-CoA:lysophospholipid acyltransferase protein or gene, and of gene combinations of acyl-CoA:lysophospholipid acyltransferases, desaturases and/or elongases can be increased, so that larger amounts of the produced compounds are produced de novo, because the organisms have previously lacked this biosynthetic activity and ability before the gene(s) in question have been introduced. This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which make possible a different gene expression in the course of time, for example as a function of the degree of maturity of a seed or an oil-storing tissue.

Owing to the introduction of an acyl-CoA:lysophospholipid acyltransferase, desaturase and/or elongase gene or several acyl-CoA:lysophospholipid acyl-transferase, desaturase and/or elongase genes into an organism or a cell, alone or in combination with other genes in an organism or a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fine chemicals (eg. fatty acids, oils, polar and neutral lipids), can be increased, so that the concentration of these precursors, cofactors or intermediates within the cells or within the storage compartment is increased, whereby the ability of the cells to produce PUFAs as described below is enhanced further. Fatty acids and lipids are themselves desirable as fine chemicals; by optimizing the activity or increasing the number of one or more acyl-CoA:lysophospholipid acyltransferases, desaturases and/or elongases which are involved in the biosynthesis of these compounds, or by destroying the activity of one or more desaturases which are involved in the degradation of these compounds, an enhanced yield, production and/or efficiency of production of fatty acid and lipid molecules in organisms, advantageously in plants, is made possible.

The isolated nucleic acid molecules used in the process according to the invention code proteins or parts of these, where the proteins or the individual protein or parts thereof comprise(s) an amino acid sequence with sufficient homology to an amino acid sequence which is shown in the sequences SEQ ID NO: 2, SEQ ID NO: 4 or SEQ ID NO: 6 so that the protein or the part thereof retains an acyl-CoA:lysophospholipid acyltransferase activity. The protein or part thereof which is coded by the nucleic acid molecule preferably retains its essential enzymatic activity and the ability of participating in the metabolism of compounds required for the synthesis of cell membranes or lipid bodies in organisms, advantageously in plants, or in the transport of molecules across these membranes. Advantageously, the protein coded by the nucleic acid molecules has at least approximately 40%, preferably at least approximately 60%, especially preferably at least approximately 70%, 80% or 90% and most preferably at least approximately 95%, 96%, 97%, 98%, 99% or more homology with an amino acid sequence an shown in SEQ ID NO: 2, SEQ ID NO: 4 or SEQ ID NO: 6. For the purposes of the invention, homology or homologous is understood as meaning identity or identical, respectively.

Essential enzymatic activity of the acyl-CoA:lysophospholipid acyltransferases used is understood as meaning that they retain an enzymatic activity of at least 10%, preferably at least 20%, especially preferably at least 30% and very especially preferably at least 40% in comparison with the proteins/enzymes coded by the sequence of SEQ ID NO: 1, SEQ ID NO: 3 or SEQ ID NO: 5 and their derivatives and can thus participate in the metabolism of compounds required for the synthesis of fatty acids in an organism, advantageously a plant cell, or in the transport across membranes, meaning desaturated $C_{16}$-, $C_{18}$-, $C_{20}$- or $C_{24}$-carbon chains with double bonds at least two, advantageously three, four or five positions.

Nucleic acids which can advantageously be used in the process are derived from fungi or plants such as algae or mosses such as the genera *Physcomitrella, Thraustochytrium, Phytophtora, Ceratodon, Isochrysis, Aleurita, Muscarioides, Mortierella, Borago, Phaeodactylum, Crypthecodinium* or from nematodes such as *Caenorhabditis*, specifically from the genera and species *Physcomitrella patens, Phytophtora infestans, Ceratodon purpureus, Isochrysis galbana, Aleurita farinosa, Muscarioides viallii, Mortierella alpina, Borago officinalis, Phaeodactylum tricornutum* or especially advantageously from *Ostreococcus tauri* or *Mantoniella squamata*.

Alternatively, the isolated nucleotide sequences used which code for acyl-CoA:lysophospholipid acyltransferases are capable of hybridizing with a nucleotide sequence of SEQ ID NO: 1, SEQ ID NO: 3 or SEQ ID NO: 5, for example under stringent conditions.

The nucleic acid sequences used in the process are advantageously introduced into the organism in question, into an expression cassette which makes possible the expression of the nucleic acids in organisms such as microorganisms or plants.

In doing so, the nucleic acid sequences which code for the inventive acyl-CoA:lysophospholipid acyltransferases, the desaturases, and/or the elongases used are linked operatively with one or more regulatory signals, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it is expressed and/or overexpressed immediately. For example, these regulatory sequences take the form of sequences to which inductors or repressors bind, thus controlling the expression of the nucleic acid. In addition to these novel regulatory sequences, or instead of these sequences, the natural regulatory elements of these sequences may still be present before the actual structural genes and, if appropriate, may have been genetically modified in such a way that their natural regulation is eliminated and the expression of the genes is enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promoter with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence. Additional advantageous sequences, such as further regulatory elements or terminator sequences, may also be inserted at the 3' end of the DNA sequences. The acyl-CoA:lysophospholipid acyltransferase genes and the Δ4-desaturase, Δ5-desaturase, Δ6-desaturase, and/or the Δ8-desaturase and/or the Δ5-elongase, Δ6-elongase and/or Δ9-elongase genes which are used advantageously may be present in one or more copies of the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the host genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

A further embodiment of the invention is one or more gene constructs which contain one or more sequences which are defined by SEQ ID NO: 1, SEQ ID NO: 3, SEQ ID NO: 5, or its derivatives and which code polypeptides as shown in SEQ ID NO: 2, SEQ ID NO: 4 and SEQ ID NO: 6. The abovementioned acyl-CoA:lysophospholipid acyltransferases lead advantageously to a substitution of the fatty acids between the cell's mono-, di- and triglyceride pool and the CoA/fatty acid ester pool, the substrate advantageously having one, two, three, four or five double bonds and advantageously 16, 18, 20, 22 or 24 carbon atoms in the fatty acid molecule. The same applies to their homologs, derivatives or analogs, which are linked operatively with one or more regulatory signals, advantageously for enhancing gene expression.

Advantageous regulatory sequences for the novel process are present for example in promoters such as the cos, tac, trp, tet, trp-tet, lpp, lac, lpp-lac, lacIq, T7, T5, T3, gal, trc, ara, SP6, λ-PR or λ-PL promoter and are advantageously employed in Gram-negative bacteria Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzene-sulfonamide-inducible), Gatz et al. Plant J. 2, 1992, 397-404 (tetracycline-inducible), EP-A-0 335 528 (abscisic acid-inducible) or WO 93/21334 (ethanol- or cyclo-hexenol-inducible). Further suitable plant promoters are the cytosolic FBPase promoter or the ST-LSI promoter of potato (Stockhaus et al., EMBO J. 8, 1989, 2445), the *Glycine max* phosphoribosylpyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (Arabidopsis oleosin promoter), U.S. Pat. No. 5,504,200 (*Phaseolus vulgaris* phaseolin promoter), WO 91/13980 (Brassica Bce4 promoter), by Baeumlein et al., Plant J., 2, 2, 1992, 233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural promoters together with their regulatory sequences, such as those mentioned above, for the novel process. It is also possible and advantageous to use synthetic promoters, either in addition or alone, in particular when they mediate seed-specific expression, such as those described in WO 99/16890.

In order to achieve a particularly high PUFA content, especially in transgenic plants, the PUFA biosynthesis genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageously preferred promoters are listed hereinbelow: USP (=unknown seed protein) and vicilin (*Vicia faba*) [Bäumlein et al., Mol. Gen. Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumin B4 (LegB4 promoter) [Bäumlein et al., Plant J., 2, 2, 1992 233-9], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which code acyl-CoA:lysophospholipid acyltransferase, the advantageous Δ4-desaturase, Δ5-desaturase, Δ6-desaturase, Δ8-desaturase and/or Δ5-elongase, Δ6-elongase and/or Δ9-elongase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator sequence. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS1 terminator sequence. As is the case with the promoters, different terminator sequences should be used for each gene.

As described above, the gene construct can also comprise further genes to be introduced into the organisms. It is possible and advantageous to introduce into the host organisms, and to express therein, regulatory genes such as genes for inductors, repressors or enzymes which, owing to their enzyme activity, engage in the regulation of one or more genes of a biosynthesis pathway. These genes can be of heterologous or of homologous origin. Moreover, further biosynthesis genes of the fatty acid or lipid metabolism can advantageously be present in a nucleic acid construct, or gene construct; however, these genes can also be positioned on one or more further nucleic acid constructs. Biosynthesis genes of the fatty acid or lipid metabolism which are advantageously used is a gene selected from the group consisting of acyl-CoA dehydrogenase(s), acyl-ACP [=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxy-genases, triacylglycerol lipases, allenoxide synthases, hydroperoxide lyases or fatty acid elongase(s) or combinations thereof. Especially advantageous nucleic acid sequences are biosynthesis genes of the fatty acid or lipid metabolism selected from the group consisting of the $\Delta 4$-desaturase, $\Delta 5$-desaturase, $\Delta 6$-desaturase, $\Delta 8$-desaturase, $\Delta 9$-desaturase, $\Delta 12$-desaturase, $\Delta 5$-elongase, $\Delta 6$-elongase or $\Delta 9$-elongase genes.

In this context, the abovementioned desaturases can be cloned into expression cassettes, according to the invention, in combination with other elongases and desaturases, and used for transforming plants with the aid of *Agrobacterium*.

Here, the regulatory sequences or factors can, as described above, preferably have a positive effect on, and thus enhance, the expression genes which have been introduced. Thus, enhancement of the regulatory elements can advantageously take place at the transcriptional level, by using strong transcription signals such as promoters and/or "enhancers". Besides, an enhancement of translation is also possible, for example by improving the stability of the mRNA. In principle, the expression cassettes can be used directly for introduction into the plants or else be introduced into a vector.

These advantageous vectors, preferably expression vectors, contain the nucleic acids which are used in the process and which code for acyl-CoA:lysophospholipid acyltransferases, or a nucleic acid construct which comprises the nucleic acid used alone or in combination with further biosynthetic genes of the fatty acid or lipid metabolism such as $\Delta 4$-desaturase, $\Delta 5$-desaturase, $\Delta 6$-desaturase, $\Delta 8$-desaturase, $\Delta 9$-desaturase, $\Delta 12$-desaturase, $\Delta 5$-elongase, $\Delta 6$-elongase and/or $\Delta 9$-elongase genes. As used in the present context, the term "vector" refers to a nucleic acid molecule which is capable of transporting another nucleic acid to which it is bound. One type of vector is a "plasmid", which means a circular double-stranded DNA loop into which additional DNA segments can be ligated. A further type of vector is a viral vector, where additional DNA segments can be ligated into the viral genome. Certain vectors are capable of autonomous replication in a host cell into which they have been introduced (for example bacterial vectors with bacterial origin of replication). Other vectors are advantageously integrated into the genome of a host cell when they are introduced into the host cell, thereby replicating together with the host genome. In addition, certain vectors are capable of controlling the expression of genes with which they are operatively linked. These vectors are referred to as "expression vectors" in the present context. Usually, expression vectors which are suitable for recombinant DNA techniques take the form of plasmids. In the present description, "plasmid" and "vector" can be used interchangeably since the plasmid is the most frequently used vector form. However, the invention is also intended to encompass other forms of expression vectors, such as viral vectors, which exert similar functions. The term "vector" is also intended to encompass other vectors which are known to the skilled worker, such as phages, viruses such as SV40, CMV, TMV, transposons, IS elements, phasmids, phagemids, cosmids, linear or circular DNA.

The recombinant expression vectors which are advantageously used in the process comprise the nucleic acids described hereinbelow or the gene construct described hereinabove in a form which is suitable for expression of the nucleic acids used in a host cell, which means that the recombinant expression vectors comprise one or more regulatory sequences, selected on the basis of the host cells to be used for the expression, which is operatively linked with the nucleic acid sequence to be expressed. In a recombinant expression vector, "operatively linked" means that the nucleotide sequence of interest is bound to the regulatory sequence(s) in such a way that the expression of the nucleotide sequence is possible and that they are bound to one another in such a way that the two sequences exert the predicted function which is allocated to the sequence (for example in an in-vitro transcription/translation system or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for the expression of acyl-CoA:lysophospholipid acyltransferases, desaturases, and elongases in prokaryotic or eukaryotic cells. This is advantageous since intermediate steps of the vector construction are frequently carried out in microorganisms for the sake of simplicity. For example, the acyl-CoA: lysophospholipid acyltransferase, desaturase and/or elongase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Cohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) Plant Cell Rep. 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) und pRIT5 (Pharmacia, Piscataway, N.J.), where glutathione S-transferase (GST), maltose-E binding protein and protein A, respectively, is fused with the recombinant target protein.

Examples of suitable inducible nonfusion E. coli expression vectors are, inter alia, pTrc (Amann et al. (1988) Gene 69:301-315) and pET 11d (Studier et al., Gene Expression Technology Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example, in E. coli pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in Streptomyces pIJ101, pIJ364, pIJ702 or pIJ361, in Bacillus pUB110, pC194 or pBD214, in Corynebacterium pSA77 or pAJ667.

In a further embodiment, the expression vector is a yeast expression vector. Examples for vectors for expression in the yeast S. cerevisiae comprise pYeDesaturasec1 (Baldari et al. (1987) Embo J. 6:229-234), pMFa (Kujan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the acyl-CoA:lysophospholipid acyltransferases, desaturases and/or elongases can be expressed in insect cells using Baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170:31-39).

The abovementioned vectors offer only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook and Russell, Molecular Cloning: A Laboratory Manual, 3rd edition, Cold Spring Harbor Laboratory, Cold Spring Harbor Laboratory Press, Cold Spring Harbor, N.Y., 2001.

In a further embodiment of the process, the acyl-CoA:lysophospholipid acyltransferases, desaturases and/or elongases can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992), Plant Mol. Biol. 20:1195-1197; and Bevan, M. W. (1984), Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operatively so that each sequence can fulfill its function, such as transcriptional termination, for example polyadenylation signals. Preferred polyadenylation signals are those which are derived from Agrobacterium tumefaciens T-DNA, such as gene 3 of the Ti plasmid pTiACH5 (Gielen et al., EMBO J. 3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operatively, such as translation enhancers, for example the overdrive sequence, which enhances the tobacco mosaic virus 5'-untranslated leader sequence, which increases the protein/RNA ratio (Gallie et al., 1987, Nucl. Acids Research 15:8693-8711).

As described above, the gene to be expressed must be linked operatively with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028.

Other preferred sequences for use in operable linkage in plant gene expression cassettes are targeting sequences, which are required for targeting the gene product into its corresponding cell compartment, for example into the vacuole, into the nucleus, all types of plastids, such as amyloplasts, chloroplasts, chromoplasts, the extracellular space, the mitochondria, the endoplasmic reticulum, elaioplasts, peroxisomes and other compartments of plant cells, (see a review in Kermode, Crit. Rev. Plant Sci. 15, 4 (1996) 285-423 and references cited therein).

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S.

Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumin B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

Other promoters which are likewise especially suitable are those which bring about a plastid-specific expression, since plastids constitute the compartment in which the precursors and some end products of lipid biosynthesis are synthesized. Suitable promoters, are the viral RNA polymerase promoter, described in WO 95/16783 and WO 97/06250, and the clpP promoter from *Arabidopsis*, described in WO 99/46394.

In particular, it may be desired to bring about the multiparallel expression of the acyl-CoA:lysophospholipid acyltransferases used in the process alone or in combination with desaturases and/or elongases. Such expression cassettes can be introduced via the simultaneous transformation of a plurality of individual expression constructs or, preferably, by combining a plurality of expression cassettes on one construct. A plurality of vectors can also, be transformed with in each case a plurality of expression cassettes and then transferred into the host cell.

Vector DNA can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acids (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook and Russell (Molecular Cloning: A Laboratory Manual., 3rd ed., Cold Spring Harbor Laboratory, Cold Spring Harbor Laboratory Press, Cold Spring Harbor, N.Y., 2001) and other laboratory textbooks such as Methods in Molecular Biology, 1995, Vol. 44, *Agrobacterium* protocols, Ed.: Gartland and Davey, Humana Press, Totowa, N.J.

Host cells which are suitable in principle for taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially preferably plants, very especially preferably plants such as oil crops, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassaya, pepper, *Tagetes*, Solanacea plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crops such as soybean, peanut, oilseed rape, canola, linseed, hemp, evening primrose, sunflower, safflower, trees (oil palm, coconut).

The invention furthermore relates to the above-described isolated nucleic acid sequences which code polypeptides with acyl-CoA:lysophospholipid acyltransferase activity, where the acyl-CoA:lysophospholipid acyltransferases encoded by the nucleic acid sequences specifically convert $C_{16}$-, $C_{18}$-, $C_{20}$- and $C_{22}$-fatty acids with at least one double bond in the fatty acid molecule.

Advantageous isolated nucleic acid sequences are sequences selected from the group consisting of:
d) a nucleic acid sequence with the sequence shown in SEQ ID NO: 1, SEQ ID NO: 3 or SEQ ID NO: 5,
e) nucleic acid sequences which, as the result of the degeneracy of the genetic code, can be derived from the coding sequence shown in SEQ ID NO: 1, SEQ ID NO: 3 or SEQ ID NO: 5
f) derivatives of the nucleic acid sequence shown in SEQ ID NO: 1, SEQ ID NO: 3 or SEQ ID NO: 5 which code for polypeptides with the amino acid sequence shown in SEQ ID NO: 2, SEQ ID NO: 4 or SEQ ID NO: 6 and which have at least 40% homology at the amino acid level with the amino acid sequence shown in SEQ ID NO: 2, SEQ ID NO: 4 or SEQ ID NO: 6 and which have an acyl-CoA:lysophospholipid acyltransferase activity.

The abovementioned nucleic acid sequences according to the invention are derived from organisms such as animals, ciliates, fungi, plants such as algae or dinoflagellates which are capable of synthesizing PUFAs. The nucleic acid sequences according to the invention are preferably derived from *Ostreococcus tauri* or *Mantonella squamata*.

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separate from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated acyl-CoA:lysophospholipid acyltransferase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process, for example a nucleic acid molecule with a nucleotide sequence of SEQ ID NO: 1, SEQ ID NO: 3 or SEQ ID NO: 5 or a part thereof can be isolated using molecular-biological standard techniques and the sequence information provided herein.

Also, for example a homologous sequence or homologous, conserved sequence regions can be identified at the DNA or amino acid level with the aid of comparative algorithms. They can be used as hybridization probe in standard hybridization techniques (such as, for example, those described in Sambrook and Russell, Molecular Cloning: A Laboratory Manual. 3rd ed., Cold Spring Harbor Laboratory, Cold Spring Harbor Laboratory Press, Cold Spring Harbor, N.Y., 2001) for isolating further nucleic acid sequences which can be used in the process. Moreover, a nucleic acid molecule comprising a complete sequence of SEQ ID NO: 1, SEQ ID NO: 3 or SEQ ID NO: 5 or a part thereof can be isolated by polymerase chain reaction, oligonucleotide primers being used on the basis of this sequence or parts thereof (for example a nucleic acid molecule comprising the complete sequence or a part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the nucleic acid sequences shown in SEQ ID NO: 1, SEQ ID NO: 3 or SEQ ID NO: 5 or with the aid of the amino acid sequences detailed in SEQ ID NO: 2, SEQ ID NO: 4 or SEQ ID NO: 6. A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis.

Homologs of the acyl-CoA:lysophospholipid acyltransferase nucleic acid sequences used, with the sequence SEQ ID NO: 1, SEQ ID NO: 3 or SEQ ID NO: 5, means, for example, allelic variants with at least approximately 40 to 60%, preferably at least approximately 60 to 70%, more preferably at least approximately 70 to 80%, 80 to 90% or 90 to 95% and even more preferably at least approximately 95%, 96%, 97%, 98%, 99% or more homology with the nucleotide sequences shown in SEQ ID NO: 1, SEQ ID NO: 3 or SEQ ID NO: 5 or their homologs, derivatives or analogs or parts thereof. Furthermore comprised are isolated nucleic acid molecules of a nucleotide sequence which hybridizes with one of the nucleotide sequences shown in SEQ ID NO: 1, SEQ ID NO: 3 or SEQ ID NO: 5 or with a part thereof, for example under stringent conditions. Allelic variants comprise in particular functional variants which can be obtained by deletion, insertion or substitution of nucleotides from/into the sequence detailed in SEQ ID NO: 1, SEQ ID NO: 3 or SEQ ID NO: 5, it being intended, however, that the enzyme activity of the resulting proteins is essentially retained.

Homologs of SEQ ID NO: 1, SEQ ID NO: 3 or SEQ ID NO: 5 mean for example also bacterial, fungal and plant homologs, truncated sequences, single-stranded DNA or RNA of the coding and noncoding DNA sequence.

Homologs of SEQ ID NO: 1, SEQ ID NO: 3 or SEQ ID NO: 5 also mean derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

The abovementioned nucleic acid molecules which code for proteins with acyl-CoA:lysophospholipid acyltransferase activity and which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed oil or flax, *Brassica* species such as oilseed rape, canola and turnip rape, pepper, sunflower, borage, evening primrose and *Tagetes*, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, New York, and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool. This is made possible by the acyl-CoA:lysophospholipid acyltransferases according to the invention. Moreover, these enzymes are capable of transferring the elongated fatty acids from the CoA esters back to the phospholipids. If appropriate, this reaction sequence can be followed repeatedly (see FIG. 4).

Examples of precursors for the biosynthesis of PUFAs are oleic acid, linoleic acid and linolenic acid. The $C_{18}$-carbon fatty acids must be elongated to $C_{20}$ and $C_{22}$ in order to obtain fatty acids of the eicosa and docosa chain type. With the aid of the acyl-CoA:lysophospholipid acyltransferases used in the process, preferably in combination with desaturases such as the Δ4-, Δ5-, Δ6- and Δ8-desaturases and/or the Δ5-, Δ6-, Δ9-elongases, arachidonic acid, eicosapentaenoic acid, docosapentaenoic acid or docosahexaenoic acid and various other long-chain PUFAs can be produced, extracted and employed in various applications regarding foodstuffs, feedstuffs, cosmetics or pharmaceuticals. Using the above-mentioned enzymes, it is possible to produce preferably $C_{18}$-, $C_{20}$- and/or $C_{22}$-fatty acids with at least two, advantageously at least three, four, five or six double bonds in the fatty acid molecule preferably up to $C_{20}$- and/or $C_{22}$-fatty acids with advantageously three, four or five double bonds in the fatty acid molecule. Desaturation may take place before or after elongation of the fatty acid in question. This is why the products of the desaturase activities and the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the acyl-CoA:lysophospholipid acyltransferases used in the process according to the invention are $C_{16}$-, $C_{18}$-, $C_{20}$- or $C_{22}$-fatty acids such as, for example, palmitic acid, palmitoleic acid, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or, arachidonic acid, respectively, eicosatetraenoic acid or eicosapentaenoic acid. The $C_{18}$-, $C_{20}$- or $C_{22}$-fatty acids with at least two double bonds in the fatty acids are obtained in the process according to the invention in the form of the free fatty acid or in the form of their esters, for example in the form of their glycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the process according to the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

For publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engeneering, Ed.: JK Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engeneering, Ed.: JK Setlow, 18:111-13; Gerhardt, 1992, Prog. Lipid R. 31:397-417; Guhnemann-Schafer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal 13(1):1-16.

The PUFAs produced in the process comprise a group of molecules which higher animals are no longer capable of synthesizing themselves (in sufficient quantity) and must therefore take up (additional quantities), although they can be synthesized readily by other organisms such as bacteria.

For the purposes of the invention, the term "acyl-CoA: lysophospholipid acyltransferases" comprises proteins which are involved in the transfer of the phospholipid-bound fatty acids into the CoA-ester pool and vice versa, and their homologs, derivatives or analogs. Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. For the purposes of the invention, the term acyl-CoA:lysophospholipid acyltransferase nucleic acid sequence(s) comprises nucleic acid sequences which code for an acyl-CoA:lysophospholipid acyltransferase, in particular an acyl-CoA:lysophosphatidylcholine acyltransferase, and which can comprise a coding region and, if appropriate, suitable 5'- and 3'-untranslated sequence regions.

In a further embodiment, derivatives of the nucleic acid molecule according to the invention, which is shown in SEQ ID NO: 1, SEQ ID NO: 3 or SEQ ID NO: 5, code for proteins with at least 40%, advantageously approximately 50 to 60%, preferably at least approximately 60 to 70% and especially preferably at least approximately 70 to 80%, 80 to 90%, 90 to 95% and most preferably at least approximately 96%, 97%, 98%, 99% or more homology (=identity) with a complete amino acid sequence of SEQ ID NO: 2, SEQ ID NO: 4 or SEQ ID NO: 6. The homology was calculated over the entire amino acid or nucleic acid sequence region. The program PileUp (J. Mol. Evolution., 25, 351-360, 1987, Higgins et al., CABIOS, 5 1989: 151-153) or the programs Gap and BestFit [Needleman and Wunsch J. Mol. Biol. 48; 443-453 (1970) and Smith and Waterman Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program BestFit and the following settings: Gap Weight: 8, Length Weight: 2.

Moreover, the invention comprises nucleic acid molecules which differ from one of the nucleotide sequences shown in SEQ ID NO: 1, SEQ ID NO: 3 or SEQ ID NO: 5 (and parts thereof) owing to the degeneracy of the genetic code and which thus code the same acyl-CoA:lysophospholipid acyltransferase as those coded by the nucleotide sequences shown in SEQ ID NO: 1, SEQ ID NO: 3 or SEQ ID NO: 5.

In addition to the acyl-CoA:lysophospholipid acyltransferase nucleotide sequences shown in SEQ ID NO: 1, SEQ ID NO: 3 or SEQ ID NO: 5, the skilled worker will recognize that DNA sequence polymorphisms which lead to changes in the amino acid sequences of the acyl-CoA:lysophospholipid acyltransferases may exist within a population. These genetic polymorphisms in the acyl-CoA:lysophospholipid acyltransferase gene may exist between individuals within a population owing to natural variation. These natural variants usually bring about a variance of 1 to 5% in the nucleotide sequence of the acyl-CoA:lysophospholipid acyltransferase gene. Each and every one of these nucleotide variations and resulting amino acid polymorphisms in the acyl-CoA:lysophospholipid acyltransferase which are the result of natural variation and do not modify the functional activity of the acyl-CoA:lysophospholipid acyltransferase are to be encompassed by the invention.

Owing to their homology to the acyl-CoA:lysophospholipid acyltransferase nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are at least 15 nucleotides in length and which hybridize under stringent conditions with the nucleic acid molecules which comprise a nucleotide sequence of SEQ ID NO: 1, SEQ ID NO: 3 or SEQ ID NO: 5. Nucleic acids with at least 25, 50, 100, 200 or more nucleotides can also be used. The "hybridizes under stringent conditions" as used in the present context is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least 75% or more homology to one another usually remain hybridized to one another. These stringent conditions are known to the skilled worker and described in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the temperature is, depending on the type of nucleic acid, between 42° C. and 58° C. in aqueous buffer with a concentration of 0.1 to 5×SSC (pH 7.2). If organic solvents, for example 50% formamide, are present in the above-mentioned buffer, the temperature under standard conditions is approximately 42° C. The hybridization conditions for DNA:DNA hybrids, for example, are preferably 0.1×SSC and 20° C. to 45° C., preferably between 30° C. to 45° C. The hybridization conditions for DNA:RNA hybrids are, for example, preferably 0.1×SSC and 30° C. to 55° C., preferably between 45° C. to 55° C. The abovementioned hybridization temperatures are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook and Rusell, "Molecular Cloning", Cold Spring Harbor Laboratory, 2001; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the percentage of homology (=identity) of two amino acid sequences (for example one of the sequences of SEQ ID NO: 2, SEQ ID NO: 4 or SEQ ID NO: 6) or of two nucleic acid sequences (for example SEQ ID NO: 1, SEQ ID NO: 3 or SEQ ID NO: 5) the sequences are written one under the other for an optimal comparison (for example, gaps may be introduced into the sequence of a protein or of a nucleic acid in order to generate an optimal alignment with the other protein or the other nucleic acid). Then, the amino acid residue or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of identical positions which the sequences share (i.e. % homology=number of identical positions/total number of positions ×100). The terms homology and identity are therefore to be considered as synonymous. The programs or algorithms specified above are used.

An isolated nucleic acid molecule which codes an acyl-CoA:lysophospholipid acyltransferase which is homologous to a protein sequence of SEQ ID NO: 2, SEQ ID NO: 4 or SEQ ID NO: 6 can be generated by introducing one or more nucleotide substitutions, additions or deletions in/into a nucleotide sequence of SEQ ID NO: 1, SEQ ID NO: 3 or SEQ ID NO: 5 so that one or more amino acid substitutions, additions or deletions are introduced in/into the protein which is coded. Mutations in one of the sequences of SEQ ID NO: 1, SEQ ID NO: 3 or SEQ ID NO: 5 can be introduced by standard techniques such as site-specific mutagenesis and PCR-mediated mutagenesis. It is preferred to generate conservative amino acid substitutions in one or more of the predicted nonessential amino acid residues. In a "conservative amino acid substitution", the amino acid residue is replaced by an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in an acyl-CoA:lysophospholipid acyltransferase is thus preferably replaced by another amino acid residue from the same family of side chains. In another embodiment, the mutations can, alternatively, be introduced randomly over all or part of the sequence encoding the acyl-CoA:lysophospholipid acyltransferase for example by saturation mutagenesis, and the resulting mutants can be screened for the herein-described acyl-CoA:lysophospholipid acyltransferase activity in order to identify mutants which have retained the acyl-CoA:lysophospholipid acyltransferase activity. Following the mutagenesis of one of the sequences SEQ ID NO: 1, SEQ ID NO: 3 or SEQ ID NO: 5, the protein which is coded can be expressed recombinantly, and the activity of the protein can be determined, for example using the tests described in the present text.

The present invention is illustrated in greater detail by the examples which follow, which are not to be construed as limiting. The content of all of the references, patent applications, patents and published patent applications cited in the present patent application is herewith incorporated by reference.

EXAMPLES

Example 1

General Methods a) General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells and yeast cells, bacterial cultures and the sequence analysis of recombinant DNA were carried out as described by Sambrook and Russell (2001) (Cold Spring Harbor Laboratory Press: ISBN 0-87969-309-6) or Kaiser, Michaelis and Mitchell (1994) "Methods in Yeast Genetics" (Cold Spring Harbor Laboratory Press: ISBN 0-87969-451-3).

b) Chemicals

Unless otherwise specified in the text, the chemicals used were obtained in analytical-grade quality from Fluka (Neu-Ulm), Merck (Darmstadt), Roth (Karlsruhe), Serva (Heidelberg) and Sigma (Deisenhofen). Solutions were prepared using pure pyrogen-free water, hereinbelow referred to as H$_2$O, from a Milli-Q-Wassersystem water purification system (Millipore, Eschborn). Restriction endonucleases, DNA-modifying enzymes and molecular biology kits were obtained from AGS (Heidelberg), Amersham (Brunswick), Biometra (Göttingen), Roche (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). Unless otherwise specified, they were used following the manufacturer's instructions.

Example 2

Cloning of an Acyltransferase Gene from *Ostreococcus tauri*

The search for conserved regions in the protein sequences of the previously isolated LPCAT from *C. elegans* (WO 2004/76617) allowed the identification of a sequence with corresponding motifs in an *Ostreococcus* sequence database (genomic sequences) (see FIG. 1). The sequence was the following:

| Name of gene | SEQ ID No.: | Amino acids |
|---|---|---|
| OtLPCAT | 2 | 239 |

The gene which codes for this protein was cloned as follows:

40 ml of an *Ostreococcus tauri* culture in the stationary phase were centrifuged, resuspended in 100 µl of double-distilled water and stored at −20° C. The corresponding genomic DNAs were amplified with the aid of the PCR method. The corresponding primer pairs were chosen in such a way that they contained the first 20 nucleotides at the 5' end and the last 20 nucleotides at the 3' end (including stop codon) and at the 5' end additionally the yeast consensus sequence for highly efficient translation (Kozak (1986) Cell 44: 283-292).

The following primers were used:

```
5'-119-Ot-LPCAT:
ATG CTG GTC GCG CGC GTC CGA GC
(SEQ ID NO: 10)

3'-120-Ot-LPCAT-XhoI:
ACT CGA GTC ACG AGT TGT TCA CGA GGC
(SEQ ID NO: 11)
```

The positions of the primers used are shown in FIG. 1.

The amplification of the OtLPCAT DNA was carried out with in each case 1 µl of defrosted cells, 200 µM dNTPs, 2.5 U Taq polymerase and 100 pmol of each primer in a total volume of 50 µl. The PCR conditions were as follows: first denaturation for 5 minutes at 95° C., followed by 30 cycles of 30 seconds at 94° C., 1 minute at 55° C. and 2 minutes at 72° C., and a final elongation step of 10 minutes at 72° C.

Example 3

Cloning of Expression Plasmids for the Heterologous Expression of OtLPCAT in Yeasts The primer pairs were chosen in such a way that they contained the yeast consensus sequence for highly efficient translation (Kozak (1986) Cell 44: 283-292) next to the start codon. The amplification of the OtLPCAT was carried out with in each case 1 µl of cDNA, 200 µM dNTPs, 2.5 U Advantage polymerase and 100 pmol of each primer in a total volume of 50 µl. The PCR conditions were as follows: first denaturation for 5 minutes at 95° C., followed by 30 cycles of 30 seconds at 94° C., 1 minute at 55° C. and 2 minutes at 72° C., and a final elongation step of 10 minutes at 72° C.

The following oligonucleotides were used in the PCR reaction for cloning the sequence for the purposes of heterologous expression in yeasts:

| Name of gene | Primer sequence |
|---|---|
| OtLPCAT (SEQ ID No. 1) | F: 5'-accatgctggtcgcgcgcgtccg (SEQ ID NO: 15)<br>R: 5'-tcacgagttgttcacgaggc (SEQ ID NO: 16) |

*F = foward primer, R = reverse primer

The PCR products were incubated for 30 minutes at 21° C. with the yeast expression vector pYES2.1-TOPO (Invitrogen) following the manufacture's instructions. The PCR product is ligated into the vector by means of a T overhang and the activity of a topoisomerase (Invitrogen). After the incubation, *E. coli* DH5α cells are transformed. Suitable clones were identified by means of PCR, the plasmid DNA was isolated by means of Qiagen DNAeasy kit and verified by sequencing. The sequence of the resulting plasmid pYES2.1-OtLPCAT is shown in SEQ ID No. 7. The correct sequence was then transformed into the *Saccharomyces* strain IVSc1 (Invitrogen) by means of electroporation (1500 V). As a control, the blank vector pYES2.1 was transformed in parallel. Thereafter, the yeasts were plated out onto complete minimal dropout uracil medium supplemented with 2% glucose. Cells which were capable of growth without uracil in the medium thus comprised the corresponding plasmids pYES2.1 or pYES2.1 of OtLPCAT. After the selection, in each case two transformants were chosen for the further functional expression.

Example 4

Cloning OELPCAT Expression Plasmids for the Purposes of Seed-Specific Expression in Plants To transform plants, a vector based on pSUN-USP was generated.

pSUN300 is a derivative of plasmid pPZP (Hajdukiewicz, P. et. al. (1994). Plant Mol. Biol. 25:989-994). pSUN-USP originated from pSUN300, by inserting a USP promoter as EcoRI fragment into pSUN300. The USP promoter corresponds to the nucleotides 1-684 (Genbank Accession X56240), where part of the noncoding region of the USP gene is present in the promoter. The promoter fragment which is 684 base pairs in size was amplified by means of commercially available T7 standard primers (Stratagene) and with the aid of a synthesized primer via a PCR reaction following standard methods (5'-GTCGACCCGCGGACTAGTGGGCCCTCTAGACCCGGGGGATCC

GGATCTGCTGGCTATGAA-3' SEQ ID NO: 19).

The PCR fragment was cut again with EcoRI/SalI and introduced into the vector pSUN300 with OCS terminator. The polyadenylation signal is that of the octopine synthase gene from the *A. tumefaciens* Ti plasmid (ocs terminator, Genbank Accession V00088) (De Greve, H. et al. (1982) J. Mol. Appl. Genet. 1 (6): 499-511). This gave rise to the plasmid with the name pSUN-USP. The construct was used for the transformation of *Arabidopsis thaliana*, oilseed rape, tobacco and linseed.

To clone Ot-LPCAT into pSUN-USP, NotI restriction sites were inserted at the 5' and the 3' end of the coding sequence, using the following primer pair:

```
pSUN-OtLPCAT
  Forward:  5'-GCGGCCGCACCATGCTGGTCGCGCGCGTCCG
              (SEQ ID NO: 17)

Reverse:  3'-GCGGCCGCTCACGAGTTGTTCACGAGGC
              (SEQ ID NO: 18)
```

Composition of the PCR mix (50 µl):

5.00 µl template cDNA 5.00 µl 10× buffer (Advantage polymerase)+25 mM MgCl$_2$ 5.00 µl 2 mM dNTP 1.25 µl of each primer (10 pmol/µl)

0.50 µl Advantage polymerase

PCR Reaction Conditions:

Annealing temperature: 1 minute at 55° C.

Denaturation temperature: 1 minute at 94° C.

Elongation temperature: 2 minutes at 72° C.

Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding DNA fragments were excised. The DNA fragments were purified by means of Qiagen gel purification kit following the manufacturer's instructions. Thereafter, vector and PCR products were ligated. The Rapid Ligation kit from Roche was used for this purpose. The resulting plasmid pSUN-OtLPCAT was verified by sequencing.

Example 5

Functional Characterization of OtLPCAT

The OtLPCAT activity was determined after the expression of OtLPCAT in yeasts and feeding various fatty acids (FIG. 2).

Since the OtLPCAT expression should lead to an efficient substitution of the acyl substrates, the double construct pESCLeu-PpD6-PSE1 which comprises the open reading frames of a Δ6-desaturase (PpD6) and of a Δ6-elongase (PSE1) from *Physcomitrella patens* (see DE 102 19 203) was additionally prepared and transformed together with either the blank vector pYES2.1 or the vector pYES2.1-OtLPCAT. The cloning of the construct pESCLeu-PpD6-PSE1 can be seen from WO 2004/076617, whose contents are expressly referred to herewith.

Analytical techniques for determining the fatty acid composition of organisms are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH Weinheim; Belter, P. A., et al. (1988) Bio-separations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

For the OtLPCAT expression, precultures of in each case 2 ml of CMdum liquid medium supplemented with 2% (w/v) raffinose, but without uracil and leucine, were first inoculated with the selected transformants and incubated for 2 days at 30° C. and 200 rpm. 5 ml CMdum liquid medium (without uracil and leucine) supplemented with 2% raffinose, 1% (v/v) Tergitol NP-40 and 250 µM linoleic acid ($18:2^{\Delta 9,12}$) or linolenic acid ($18:3^{\Delta 9,12,15}$) were then inoculated with the precultures to an $OD_{600}$ of 0.08. The expression was induced at an $OD_{600}$ of 0.2-0.4 by addition of 2% (w/v) galactose. Incubation of the cultures was continued for 48 hours at 20° C.

The yeast cells from the main cultures were harvested by centrifugation (100×g, 10 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with an increment of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

FIG. 2A shows the conversion of the fed fatty acid 18:2$^{\Delta9,12}$ into 20:3$^{\Delta8,11,14}$ by yeasts which had been transformed with the plasmids pESCLeu-PpD6-PSE1 and pYES2.1. In comparison, FIG. 2B shows the conversion in yeasts which, in addition to the plasmid pESCLeu-PpD6-PSE1, additionally comprise the plasmid pYES2.1-OtLPCAT. The fed substrate was detected in large amounts in all transgenic yeasts. Both transgenic yeasts revealed a synthesis of 18:3$^{\Delta6,9,12}$ and 20:3$^{\Delta8,11,14}$, the products of the Δ-6-desaturase and Δ-6-elongase reactions. This means that the genes PpD6 and PSE1 were expressed functionally.

In the control yeasts, which had been transformed with the vectors pESCLeu-PpD6-PSE1 and pYes2.1, the content of 20:3$^{\Delta8,11,14}$, to which 18:3$^{\Delta6,9,12}$ is elongated by PSE1, was considerably lower than in the yeasts which additionally express OtLPCAT. Indeed, the elongation of 18:3$^{\Delta6,9,12}$ was improved by 150% as the result of the additional expression of OtLPCAT (FIG. 2B). This significant increase in the LCPUFA content can only be explained as follows: the exogeneously fed fatty acid (18:2$^{\Delta9,12}$) is first incorporated into phospholipids, where it is desaturated by Δ6-desaturase to give 18:3$^{\Delta6,9,12}$. Only after re-equilibration with the acyl-CoA pool is it possible for 18:3$^{\Delta6,9,12}$ to be elongated by elongase to give 20:3$^{\Delta8,11,14}$-CoA and then to be re-incorporated into the lipids. OtLPCAT is capable of highly efficiently backconverting the Δ6-desaturated acyl groups, which are incorporated into phospholipids, into CoA-thioesters. As a result, the elongation of the fed fatty acid 18:2$^{\Delta9,12}$ is also improved (FIG. 2B).

Example 6

Cloning of Acyltransferase Genes from *Mantoniella squamata*

By searching for conserved regions in the protein sequences of the previously isolated LPCAT from *C. elegans* (WO 2004/76617), it was possible to identify sequences with corresponding motifs in a *Mantoniella* sequence database (see FIG. 1). The sequences were the following:

| Name of gene | SEQ ID No. | Amino acids |
|---|---|---|
| MsLPCAT112 | 4 | 233 |
| MsLPCAT118 | 6 | 272 |

The genes which code for these proteins were cloned as follows:

A 2 l culture of *Mantoniella squamata* was grown in f/2 medium (Guillard, R. R. L. (1975) Culture of phytoplankton for feeding marine invertebrates. In *Culture of Marine Invertebrate Animals* (Eds. Smith, W. L. and Chanley, M. H.), Plenum Press, New York, pp 29-60) for 14 days at a light intensity of 80 E/cm$^2$. After centrifugation of the cells, RNA was isolated with the aid of the RNAeasy kits from Qiagen (Valencia, Calif., US). The mRNA was subjected to reverse transcription with the Marathon cDNA amplification kit (BD Biosciences), and adaptors were ligated in accordance with the manufacturer's instructions. The cDNA library was then used for the PCR for cloning expression plasmids by means of 5'- and 3'-RACE (rapid amplification of cDNA ends).

The corresponding genomic DNAs were amplified by PCR. The corresponding primer pairs were selected in such a way that they contained the first 20 nucleotides at the 5' end and the last 20 nucleotides at the 3' end (including stop codon) and additionally the yeast consensus sequence for highly efficient translation (Kozak (1986) Cell 44: 283-292) at the 5' end.

The following primers were used:

```
5'-112-MA-LPCAT-BamHI:
AGG ATC CAT GTC TTT TTA CCT CGT CAC CTT
CAC C(SEQ ID NO: 12)

3'-113-MA-LPCAT_XhoI:
ACT CGA GTC ACG AGT ACT TGA CAA GGC
(SEQ ID NO: 13)
``` for the shorter form of the *Mantoniella squamata* LPCAT and

```
5'-118-MA-LPCAT:
ATG TCG AGG TCG ACG GTA TCG AT

3'-113-MA-LPCAT_XhoI:
ACT CGA GTC ACG AGT ACT TGA CAA GGC
``` for the longer form of the *Mantoniella squamata* LPCAT.

The positions of the primers used are shown in FIG. 1.

The amplification of the MsLPCAT DNAs was carried out with in each case 1 µl of defrosted cells, 200 µM dNTPs, 2.5 U Taq polymerase and 100 µmol of each primer in a total volume of 50 µl. The PCR conditions were as follows: first denaturation for 5 minutes at 95° C., followed by 30 cycles of 30 seconds at 94° C., one minute at 55° C. and 2 minutes at 72° C., and a final elongation step for 10 minutes at 72° C.

Example 7

Cloning of Expression Plasmids for the Purposes of Heterologous Expression of MsLPCAT in Yeasts The corresponding primer pairs were selected in such a way that they contained the yeast consensus sequence for highly efficient translation (Kozak, Cell 1986, 44:283-292) next to the start codon. The amplification of the MsLPCATs was carried out in each case with 1 µl cDNA, 200 µM dNTPs, 2.5 U Advantage polymerase and 100 pmol of each primer in a total volume of 50 µl. The PCR conditions were as follows: first denaturation for 5 minutes at 95° C., followed by 30 cycles for 30 seconds at 94° C., for 1 minute at 55° C. and for 2 minutes at 72° C. and a last elongation step for 10 minutes at 72° C.

The following oligonucleotides for the PCR reaction were used for cloning the sequence for the heterologous expression in yeasts:

| Name of gene: | Primer sequence |
|---|---|
| MsLPCAT112 (SEQ ID No. 3) | F: 5'-accatgtcttttttacctcgtcac (SEQ ID NO: 20)<br>R: 5'-tcacgagtacttgacaaggc (SEQ ID NO: 21) |
| MsLPCAT118 (SEQ ID No. 5) | F: 5'-accatgtcgaggtcgacggtatc (SEQ ID NO: 22)<br>R: 5'-tcacgagtacttgacaaggc (SEQ ID NO: 23) |

*F = forward primer, R = reverse primer

The PCR products were incubated for 30 minutes at 21° C. with the yeast expression vector pYES2.1-TOPO (Invitrogen) following the manufacturer's instructions. The PCR product is ligated into the vector by means of a T-overhang and the activity of a topoisomerase (Invitrogen). After the incubation, E. coli DH5α cells were transformed. Suitable clones were identified by PCR, the plasmid DNA was isolated by means of the Qiagen DNAeasy kit and verified by sequencing. The sequences of the resulting plasmids pYES2.1-MsLPCAT112 and pYES2.1-MsLPCAT118 are shown in SEQ ID NOs. 8 and 9, respectively. The correct sequence was then transformed into the Saccharomyces strain INVSc1 (Invitrogen) by electroporation (1500V). As a control, the blank vector pYES2.1 was transformed in parallel. Thereafter, the yeasts were plated out onto complete minimal dropout uracil medium supplemented with 2% glucose. Cells which were capable of growing in the medium without uracil thus comprised the corresponding plasmids pYES2.1, pYES2.1-MsLPCAT112 and pYES2.1-MsLPCAT118. After the selection, in each case two transformants were chosen for the further functional expression.

Example 8

Cloning Expression Plasmids for the Purposes of Seed-Specific Expression in Plants To transform plants, a further vector based on pSUN-USP was generated (see Example 4). To this end, NotI restriction sites were introduced at the 5' and 3' ends of the coding sequence, using the following primer pairs:

```
pSUN-MsLPCAT112
Forward:  5'-GCGGCCGCACCATGTCTTTTTACCTCGTCAC
          (SEQ ID NO: 24)

Reverse:  3'-GCGGCCGCTCACGAGTACTTGACAAGGC
          (SEQ ID NO: 25)

pSUN-MsLPCAT118
Forward:  5'-GCGGCCGCACCATGTCGAGGTCGACGGTATC
          (SEQ ID NO: 26)

Reverse:  3'-GCGGCCGCTCACGAGTACTTGACAAGGC
          (SEQ ID NO: 27)
```

Composition of the PCR Mix (50 µl):

5.00 µl template cDNA 5.00 µl 10× buffer (Advantage polymerase)+25 mM $MgCl_2$ 5.00 µl 2 mM dNTP 1.25 µl of each primer (10 pmol/µl)

0.50 µl Advantage polymerase (Clontech)

PCR Reaction Conditions:

Annealing temperature: 1 minute at 55° C.

Denaturation temperature: 1 minute at 94° C.

Elongation temperature: 2 minutes at 72° C.

Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding DNA fragments were excised. The DNA fragments were purified by means of Qiagen gel purification kit following the manufacturer's instructions. Thereafter, vector and PCR products were ligated. The Rapid Ligation kit from Roche was used for this purpose. The resulting plasmids pSUN-MsLPCAT112 and pSUN-MsLPCAT118 were verified by sequencing.

Example 9

Functional Characterization of the MsLPCATs

The activity of the MsLPCATs was determined after expression of the MsLPCATs in yeast and the feeding of a variety of fatty acids (FIGS. 3A, B and C). As in Example 5, the construct pESCLeu-PpD6-PSE1 was again introduced into the yeasts together with the blank vector pYES2.1 or the plasmid pYES2.1-MsLPCAT112 or pYES2.1-MsLP-CAT118.

The expression of the MsLPCATs was effected as described in Example 5 for OtLPCAT.

FIG. 3A shows the conversion of the fed fatty acid $18:2^{\Delta 9,12}$ into $20:3^{\Delta 8,11,14}$ by yeasts which had been transformed with the plasmid pESCLeu-PpD6-PSE1 and pYES2.1. In comparison, FIG. 3B shows the conversion in yeasts which, in addition to the plasmid pESCLeu-PpD6-PSE1, additionally comprise the plasmid pYES2.1-MsLP-CAT112. FIG. 3C describes the fatty acid spectrum of yeasts which had been transformed with the plasmids pESCLeu-PpD6-PSE1 and pYES2.1-MsLPCAT118. The fed substrate linoleic acid (18:2) was detected in large amounts in all transgenic yeasts. All transgenic yeasts revealed a synthesis of $18:3^{\Delta 6,9,12}$ and $20:3^{\Delta 8,11,14}$, the products of the Δ6-desaturase and the Δ6-elongase reactions. This means that the genes PpD6 and Pse1 were functionally expressed.

In the control yeasts, which had been transformed with the vectors pESCLeu-PpD6-PSE1/pYes2.1, the content of $20:3^{\Delta 8,11,14}$, to which $18:3^{\Delta 6,9,12}$ is elongated by PSE1, was considerably lower than in the yeasts which additionally express one of the two MsLPCATs. Indeed, the elongation of $18:3^{\Delta 6,9,12}$ is improved by 70% (MsLPCAT112) and 160% (MsLPCAT118), respectively, as the result of the additional expression of an MsLPCAT (FIG. 3B, C). This significant increase in the LCPUFA content can only be explained as follows: the exogeneously fed fatty acid ($18:2^{\Delta 9,12}$) is first incorporated into phospholipids, where it is desaturated by Δ6-desaturase to give $18:3^{\Delta 6,9,12}$. Only after re-equilibration with the acyl-CoA pool is it possible for $18:3^{\Delta 6,9,12}$ to be elongated by elongase to give $20:3^{\Delta 8,11,14}$-CoA and then to be re-incorporated into the lipids. The MsLPCATs is capable of highly efficiently backconverting the Δ6-desaturated acyl groups into CoA-thioesters. As a result, the elongation of the fed fatty acid $18:2^{\Delta 9,12}$ is also improved (FIG. 3B, C).

Example 10

Plant Transformation and Expression of PUFA-Specific Acyltransferases in Plants The expression of LCPUFA-specific acyltransferases in transgenic plants is advantageous for increasing the LCPUFA content in these plants. To this end, the acyltransferase cDNAs according to the invention were cloned into binary vectors (see Examples 4 and 8) and transferred into *Arabidopsis thaliana*, *Brassica napus* and *Linum usitatissimum* via *Agrobacterium*-mediated DNA transfer. The expression of the acyltransferase cDNA was under the control of the seed-specific USP promoter (construction of the binary plasmid pSUN300-USP, see Example 4).

Especially preferred in this context are transgenic plants which already express the desaturases and elongases required for the synthesis of LCPUFAs and which produce small amounts of these LCPUFAs. Such plants are, for example, those which have been described in DE 102 19 203, which comprise functional genes for Δ6-desaturase, Δ6-elongase and Δ5-desaturase and which produce small amounts of ARA and EPA.

The resulting binary vectors with acyltransferase genes were transformed into *Agrobacterium tumefaciens* (Höfgen and Willmitzer (1988) Nucl. Acids Res. 16: 9877). The transformation of *A. thaliana* was accomplished by means of the floral-dip method (Clough and Bent (1998) Plant Journal 16: 735-743), the transformation of *N. tabacum* via the cocultivation of tobacco leaf segments with transformed *A. tumefaciens* cells, and the transformation of linseed and oilseed rape by cocultivation of hypocotyl segments with transformed *A. tumefaciens* cells. Suitable methods are known to the skilled person.

The expression of the acyltransferase genes in transgenic *Arabidopsis*, tobacco, oilseed rape and linseed plants was analyzed by Northern blot analysis. Selected plants were analyzed for their PUFA content in the seed oil.

The *Agrobacterium*-mediated transformation of plants can be accomplished using standard transformation and regeneration techniques (Gelvin, Stanton B., Schilperoort, Robert A., Plant Molecular Biology Manual, 2nd edition, Dordrecht: Kluwer Academic Publ., 1995, in Sect., Ringbuc Zentrale Signatur: BTI 1-P ISBN 0-7923-2731-4; Glick, Bernard R., Thompson, John E., Methods in Plant Molecular Biology and Biotechnology, B. Raton: CRC Press, 1993, 360 p., ISBN 0-8493-5164-2).

For example, oilseed rape can be transformed by cotyledon or hypocotyl trans-formation (Moloney et al. (1989) Plant Cell Report 8: 238-242; De Block et al. (1989) Plant Physiol. 91: 694-701). The use of antibiotics for the selection of agrobacteria and plants depends on the binary vector and the agrobacterial strain used for the transformation. Selection of oilseed rape is usually carried out using kanamycin as selectable plant marker. The *Agrobacterium*-mediated gene transfer in linseed (*Linum usitatissimum*) can be accomplished for example using a technique described by Mlynarova et al. (1994) Plant Cell Report 13: 282-285.

The transformation of soybean can be carried out using for example a technique described in EP-A-O 0424047 (Pioneer Hi-Bred International) or in EP-A-O 0397687, U.S. Pat. No. 5,376,543, U.S. Pat. No. 5,169,770 (University Toledo). The plant transformation using particle bombardment, polyethylene-glycol-mediated DNA uptake or via the silicon carbonate fiber technique is described for example by Freeling and Walbot "The maize handbook" (1993) ISBN 3-540-97826-7, Springer Verlag New York.

To detect fatty acids in plants, plant lipids are extracted from plant material as described by Cahoon et al. (1999) Proc. Natl. Acad. Sci. USA 96 (22):12935-12940, and Browse et al. (1986) Analytic Biochemistry 152:141-145. The qualitative and quantitative lipid or fatty acid analysis is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pages (Oily Press Lipid Library; 1); Progress in Lipid Research, Oxford: Pergamon Press, 1 (1952)-16 (1977) under the title: Progress in the Chemistry of Fats and Other Lipids CODEN.

Thus, fatty acids or triacylglycerol (=TAG, abbreviations shown in brackets) can be analyzed for example by means of fatty acid methyl ester (=FAME), gas liquid chromatography/mass spectrometry (=GC-MS) or thin-layer chromatography (TLC).

The unambiguous detection for the presence of fatty acid products can be obtained by analyzing recombinant organisms using analytical standard methods such as: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometric methods], Lipide 33:343-353).

The plant material to be analyzed can be disrupted either by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 µm, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

In the case of fatty acids for which no standards are available, the identity can be demonstrated via derivatization, followed by GC-MS analysis. For example, the localization of fatty acids with triple bond via GC-MS is carried out after derivatization with 4,4-dimethoxyoxazoline derivatives (Christie, 1998, see hereinabove).

Fatty Acid Analysis in Plants

The total fatty acids were extracted from plant seeds and analyzed by means of gas chromatography.

The seeds were taken up in 1% sodium methoxide in methanol and incubated for 20 minutes at RT (approx. 22° C.). After washing with NaCl, the FAMEs were taken up in 0.3 ml of heptane.

The samples were separated on a ZEBRON-ZB-Wax capillary column (30 m, 0.32 mm, 0.25 µm; Phenomenex) in a Hewlett Packard 6850 gas chromatograph equipped with flame ionization detector. The oven temperature was programmed from 70° C. (holding for 1 minute) to 200° C., with an increment of 20° C./min, then to 250° C. (holding for 5 minutes) with an increment of 5° C./min and finally to 260° C. with an increment of 5° C./min. The carrier gas used was nitrogen (4.5 ml/min at 70° C.). The fatty acids were identified by comparison with retention times of FAME standards (SIGMA).

From the work presented here, the function of the acyl-CoA:lysophospholipid acyltransferase can be derived as shown in FIG. 4. Thus, the biosynthetic pathway of the LCPUFAs presents itself as follows: Desaturases catalyze the introduction of double bonds into lipid-coupled fatty acids (sn2-acyl-phosphatidylcholine), while the elongases catalyze exclusively the elongation of coenzyme-A-esterified fatty acids (acyl-CoAs). According to this mechanism, the alternating effect of desaturases and elongases requires a continuous exchange of acyl substrates between phospholipids and the acyl-CoA pool, and thus the existence of an additional activity which converts the acyl substrates into the substrate form required in each case, i.e. lipids (for desaturases) or CoA-thioesters (for elongases). This exchange between acyl-CoA pool and phospholipids is made possible by LCPUFA-specific acyl-CoA:lysophospholipid acyltransferases.

EQUIVALENTS

Many equivalents of the specific embodiments according to the invention described herein can be identified or found by the skilled worker, resulting simply in routine experiments. These equivalents are intended to be within the scope of the patent claims.

DESCRIPTION OF THE FIGURES

Figure 1:
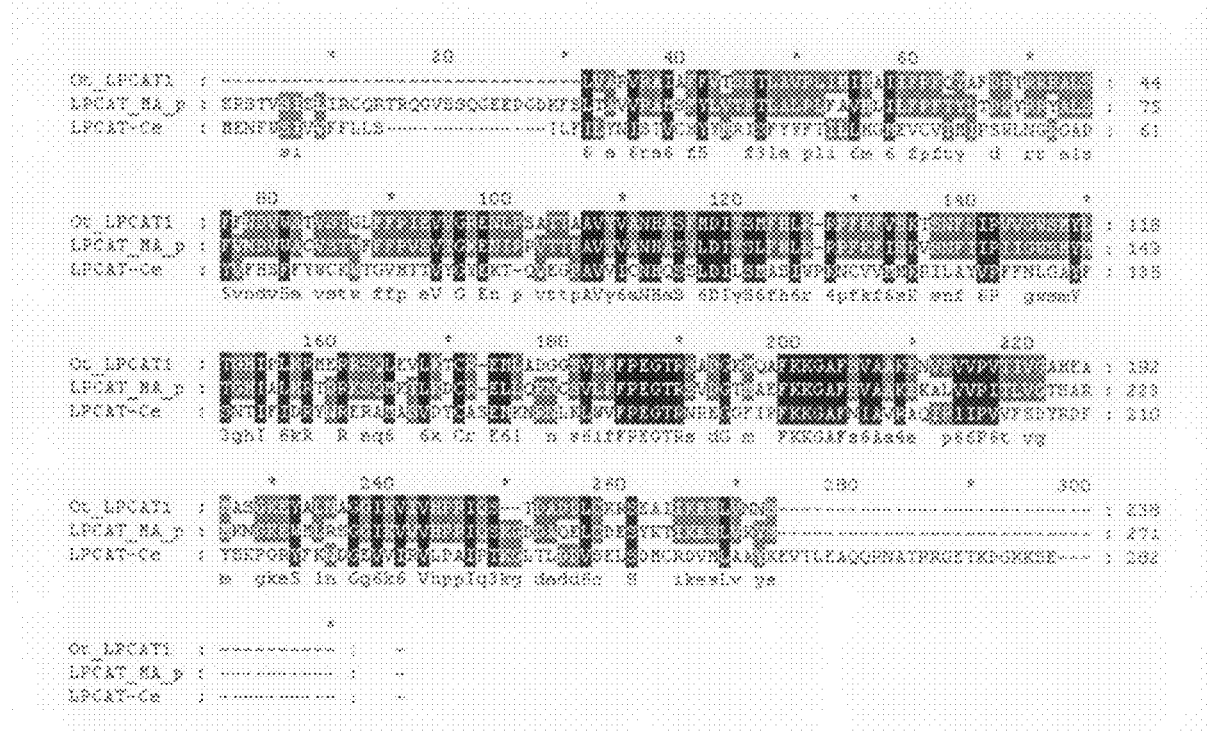

FIG. 1: Amino acid sequence alignment of OtLPCAT ("Ot_LPCAT1"; SEQ ID NO: 2), MsLPCAT ("LPCAT_MA_p"; SEQ ID NO: 6) and CeLPCAT ("LPCAT-Ce"; SEQ ID NO: 28).

Figure 2:
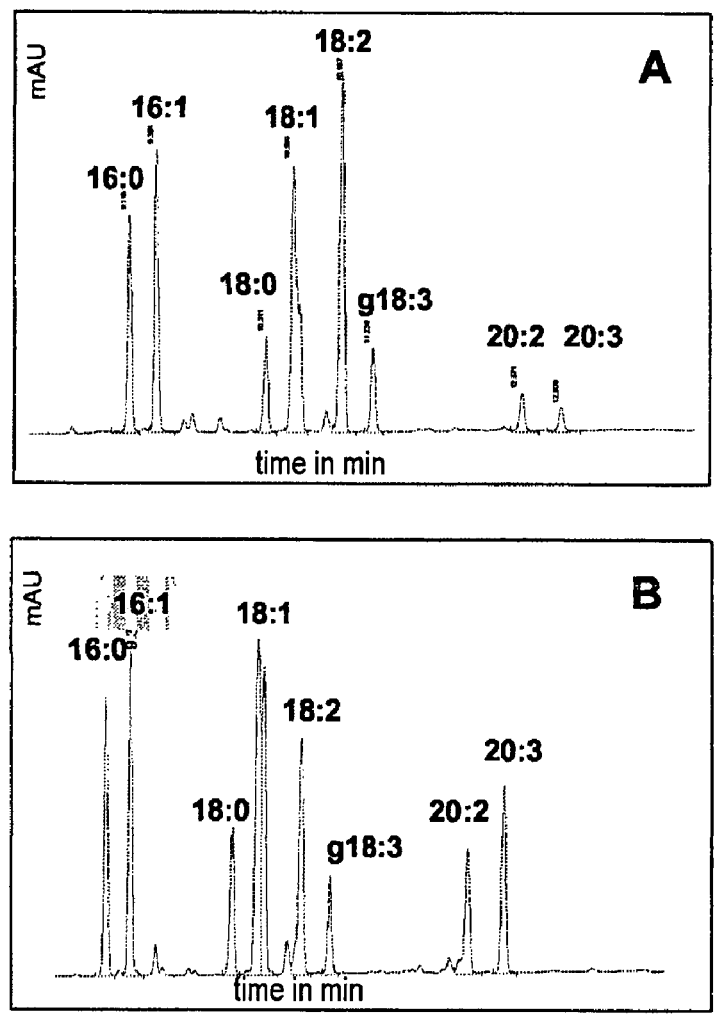
FIG. 2: Fatty acid analysis of yeasts which have been transformed with the plasmids pESCLeu-PpD6-PSE1 and pYES2.1 (A), or pLEU-PSE1 (Pp)_d6Des(Pp) and pYES2.1-OtLPCAT (B), respectively, after feeding with $18:2^{\Delta 9,12}$.
Figure 3:
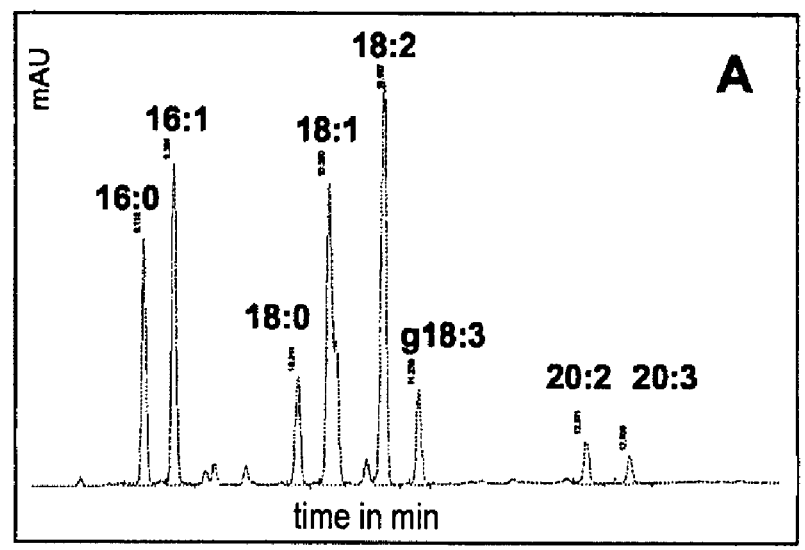
FIG. 3: Fatty acid analysis of yeasts which have been transformed with the plasmids pESCLeu-PpD6-PSE1 and pYES2.1 (A), pESCLeu-PpD6-PSE1 and pYES2.1-MsLP-CAT112 (B), or pESCLeu-PpD6-PSE1 and pYES2.1-MsLP-CAT112 (C), respectively, after feeding with $18:2^{\Delta 9,12}$.
Figure 3:
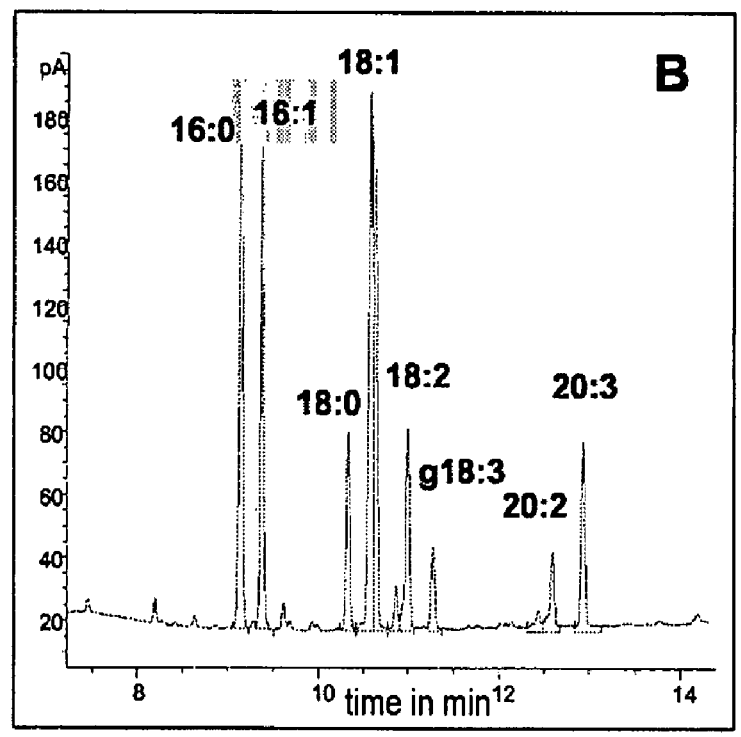
Figure 4:
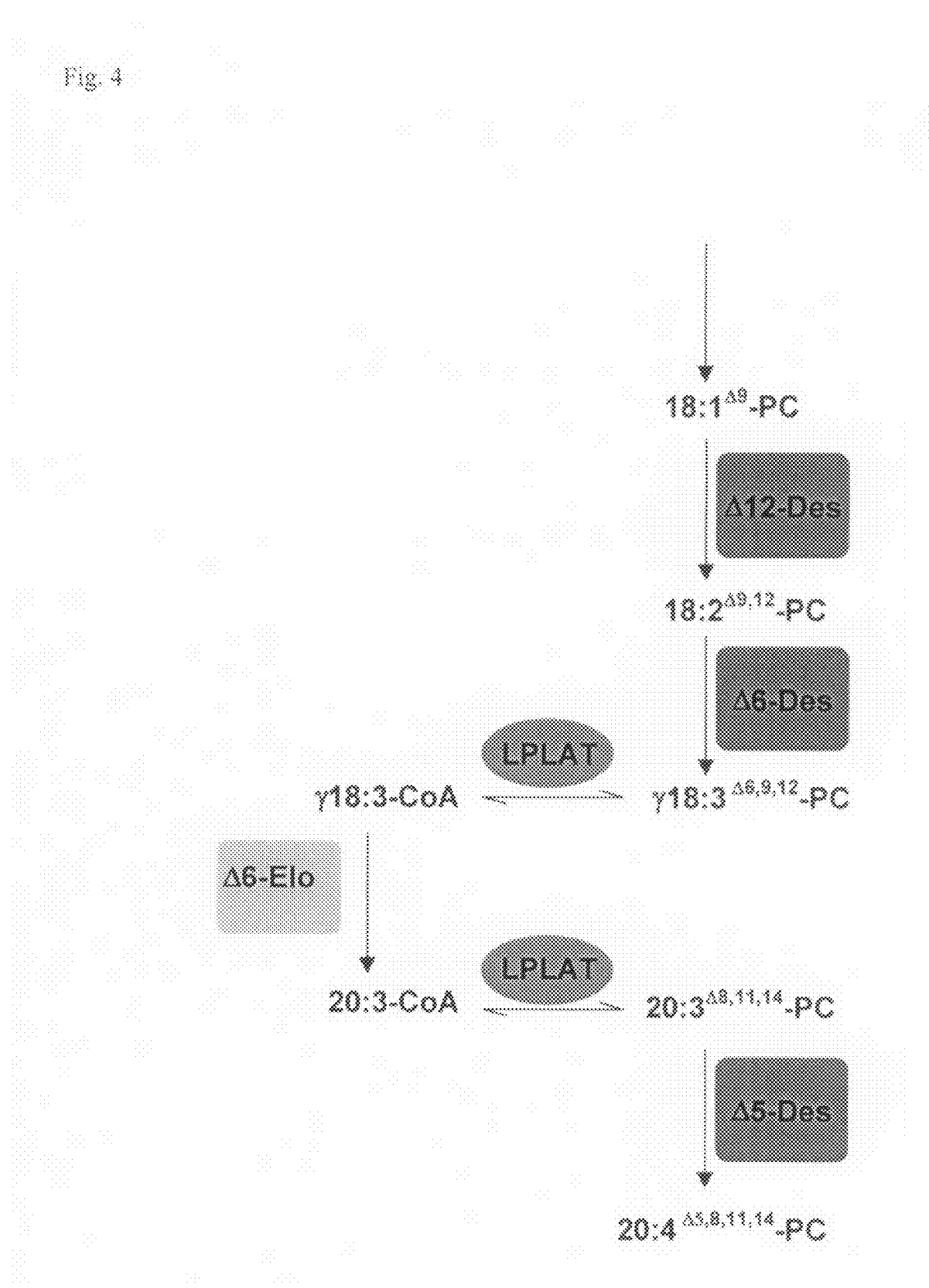
FIG. 4: Biosynthetic pathway of LCPUFAs

The invention claimed is:

1. An isolated nucleic acid molecule which codes for a polypeptide having acyl-CoA:lysophospholipid acyltransferase activity, wherein the acyl-CoA:lysophospholipid acyltransferase encoded by the isolated nucleic acid molecule specifically converts $C_{16}$-, $C_{18}$-, $C_{20}$- or $C_{22}$-fatty acids with at least one double bond in the fatty acid molecule and wherein the isolated nucleic acid molecule comprises a nucleic acid sequence selected from the group consisting of:
   a) a nucleic acid sequence with the sequence shown in SEQ ID NO: 1, SEQ ID NO: 3 or SEQ ID NO: 5,
   b) nucleic acid sequences which, as the result of the degeneracy of the genetic code, are derived from the coding sequence shown in SEQ ID NO: 1, SEQ ID NO: 3 or SEQ ID NO: 5, and
   c) nucleic acid sequences which code for polypeptides having at least 80% 95% homology at the amino acid level with the amino acid sequence shown in SEQ ID NO: 2, SEQ ID NO: 4 or SEQ ID NO: 6 and having acyl-CoMysophospholipid acyltransferase activity.

2. The isolated nucleic acid molecule according to claim 1 derived from a eukaryotic organism.

3. A gene construct containing the isolated nucleic acid molecule according to claim 1, wherein the nucleic acid sequence is operatively linked with one or more regulatory signals.

4. The gene construct according to claim 3, wherein the gene construct contains additional biosynthesis genes of the fatty acid or lipid metabolism selected from the group consisting of acyl-CoA dehydrogenase(s), acyl-ACP (acyl carrier protein) desaturase(s), acyl-ACP thioesterase(s), fatty acid acyl transferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases and fatty acid elongase(s).

5. The gene construct according to claim 3, wherein the gene construct contains additional biosynthesis genes of the fatty acid or lipid metabolism selected from the group of the Δ4-desaturase, Δ5-desaturase, Δ6-desaturase, Δ8-desaturase, Δ9-desaturase, Δ12-desaturase, Δ5-elongase, Δ6-elongase and Δ9-elongase genes.

6. A vector containing the nucleic acid molecule according to claim 1.

7. A process for producing polyunsaturated fatty acids in an organism, which comprises the following steps:
   a) introducing, into an organism, at least one nucleic acid sequence selected from the group consisting of:
      i) a nucleic acid sequence with the sequence shown in SEQ ID NO: 1, SEQ ID NO: 3 or SEQ ID NO: 5, which code for a polypeptide with an acyl-CoA: lysophospholipid acyltransferase activity;
      nucleic acid sequences which, as the result of the degeneracy of the genetic code, are derived from the coding sequence shown in SEQ ID NO: 1, SEQ ID NO: 3 or SEQ ID NO: 5; and
      iii) nucleic acid sequences which code for polypeptides having at least 95% homology at the amino acid level with the amino acid sequence shown in SEQ ID NO: 2, SEQ ID NO: 4 or SEQ ID NO: 6 and having an equivalent acyl-CoA: lysophospholipid acyltransferase activity, and
   b) culturing and harvesting the organism.

8. The process according to claim 7, wherein, in addition to the nucleic acid sequences mentioned under step a), further nucleic acid sequences which code for polypeptides of the fatty acid or lipid metabolism selected from the group consisting of acyl-CoA dehydrogenase(s), acyl-ACP (acyl carrier protein) desaturase(s), acyl-ACP thioesterase(s), fatty acid acyl transferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases and fatty acid elongase(s) are introduced into the organism.

9. The process according to claim 7, wherein, in addition to the nucleic acid sequences mentioned under step a), further nucleic acid sequences which code for polypeptides selected from the group consisting of Δ4-desaturases, Δ5-desaturases, Δ6-desaturases, Δ8-desaturases, Δ9-desaturases, Δ12-desaturases, Δ5-elongases, Δ6-elongases and Δ9-elongases are introduced into the organism.

10. The process according to claim 7, wherein $C_{16}$-, $C_{18}$-, $C_{20}$- or $C_{22}$-fatty acids are used as substrate for the acyl-CoA: lysophospholipid acyltransferases.

11. The process according to claim 7, wherein the polyunsaturated fatty acids are isolated from the organism in the form of an oil, lipid or a free fatty acid.

12. The process according to claim 7, wherein the polyunsaturated fatty acids produced in the process are $C_{18}$-, $C_{20}$- or $C_{22}$-fatty acids with at least two double bonds in the molecule.

13. The process according to claim 7, wherein a polyunsaturated fatty acid selected from the group consisting of dihomo-γ-linolenic acid, arachidonic acid, eicosapentaenoic acid, docosapentaenoic acid and docosahexaenoic acid is produced in the process.

14. The process according to claim 7, wherein the organism is a microorganism, a nonhuman animal or a plant.

15. The process according to claim 7, wherein the organism is a transgenic plant.

16. The process according to claim 7, wherein the transgenic plant is an oil crop plant.

17. A process for the preparation of feed, foodstuff, cosmetics or pharmaceuticals, comprising utilizing the oil, lipids or fatty acids produced by the process according to claim 7.

18. The isolated nucleic acid molecule according to claim 1, comprising the sequence shown in SEQ ID NO: 1, SEQ ID NO: 3 or SEQ ID NO: 5 or a nucleic acid sequence which codes for the amino acid level with the amino acid sequence shown in SEQ ID NO: 2, SEQ ID NO: 4 or SEQ ID NO: 6.

19. The process for producing polyunsaturated fatty acids in an organism according to claim 7, wherein the at least one nucleic acid sequence comprises the sequence shown in SEQ ID NO: 1, SEQ ID NO: 3 or SEQ ID NO: 5, or a nucleic acid sequence which codes for the amino acid sequence shown in SEQ ID NO: 2, SEQ ID NO: 4 or SEQ ID NO: 6.

20. An isolated nucleic acid molecule which codes for a polypeptide having acyl-CoA:lysophospholipid acyltransferase activity, wherein the acyl-CoA:lysophospholipid acyltransferase encoded by the isolated nucleic acid molecule specifically converts $C_{16}$-, $C_{18}$-, $C_{20}$- or $C_{22}$-fatty acids with at least one double bond in the fatty acid molecule and wherein the isolated nucleic acid molecule comprises a nucleic acid sequence that hybridizes to the full length of one of the nucleic acid sequences set forth in SEQ ID NO: 1, 3, or 5 under one of the following stringent conditions:
   a) hybridization in 6× sodium chloride/sodium citrate (SSC) at approximately 45° C., followed by at least one washing step in 0.2×SSC, 0.1% SDS at 65° C.;

b) hybridization in an aqueous buffer with a concentration of 0.1 to 5×SSC, pH 7.2, at 42 to 58° C., followed by at least one washing step in 0.2×SSC, 0.1% SDS at 65° C.;

c) hybridization in 0.1 to 5×SSC, in the presence of organic solvents, at approximately 42° C., followed by at least one washing step in 0.2×SSC, 0.1% SDS at 65° C.;

d) hybridization in 0.1 to 5×SSC, in the presence of 50% formamide, at approximately 42° C., followed by at least one washing step in 0.2×SSC, 0.1% SDS at 65° C.; and e) hybridization in 0.1×SSC at 20 to 55° C., followed by at least one washing step in 0.2×SSC, 0.1% SDS at 65° C.

* * * * *

UNITED STATES PATENT AND TRADEMARK OFFICE
CERTIFICATE OF CORRECTION

| | | |
|---|---|---|
| PATENT NO. | : 7,871,804 B2 | |
| APPLICATION NO. | : 11/793854 | |
| DATED | : January 18, 2011 | |
| INVENTOR(S) | : Petra Cirpus et al. | |

It is certified that error appears in the above-identified patent and that said Letters Patent is hereby corrected as shown below:

In the Claims:

In Claim 1, in column 81, on line 18, "at least 80% 95% homology" should read -- at least 95% homology --.

In Claim 1, in column 81, on line 21, "acyl-CoMysophospholipid" should read -- acyl-CoA:lysophospholipid --.

Signed and Sealed this
Twenty-seventh Day of December, 2011

David J. Kappos
*Director of the United States Patent and Trademark Office*

```
                         SEQUENCE LISTING

<160> NUMBER OF SEQ ID NOS: 28

<210> SEQ ID NO 1
<211> LENGTH: 720
<212> TYPE: DNA
<213> ORGANISM: Ostreococcus tauri
<220> FEATURE:
<221> NAME/KEY: CDS
<222> LOCATION: (1)..(720)

<400> SEQUENCE: 1 atg ctg gtc gcg cgc gtc cga gcg atc gcc ttc ttc gtc acc tcg ttc      48
Met Leu Val Ala Arg Val Arg Ala Ile Ala Phe Phe Val Thr Ser Phe
1               5                   10                  15 acg ctc gcg gtg ccg ctc atc atg atc atg gcg atc ata ttc ccg ttt      96
Thr Leu Ala Val Pro Leu Ile Met Ile Met Ala Ile Ile Phe Pro Phe
                20                  25                  30 cag tac gcg ttc gat cga acg cga agg cgg gcg ctg agt ttc ttc aac     144
Gln Tyr Ala Phe Asp Arg Thr Arg Arg Arg Ala Leu Ser Phe Phe Asn
            35                  40                  45 gac gtc tgg gcg acg gtg tcc act ggg ttg ttc ttt ccg att gaa gtc     192
Asp Val Trp Ala Thr Val Ser Thr Gly Leu Phe Phe Pro Ile Glu Val
        50                  55                  60 gtc gga cgg gag aat ttg ccg agc gcg acg acg gcg gcg gtg tac gtc     240
Val Gly Arg Glu Asn Leu Pro Ser Ala Thr Thr Ala Ala Val Tyr Val
65                  70                  75                  80 gcg aat cac gcg tcg ttc atg gat att tat tcc atg ttt cac ctg cga     288
Ala Asn His Ala Ser Phe Met Asp Ile Tyr Ser Met Phe His Leu Arg
                85                  90                  95 cgc ccg ttc aag ttt gtg tcc aag acg agc aac ttt ttg atc ccc gtc     336
Arg Pro Phe Lys Phe Val Ser Lys Thr Ser Asn Phe Leu Ile Pro Val
                100                 105                 110 gtc ggg tgg tcg atg tat ctc acg gga cac atc cct ctg aag cgc atg     384
Val Gly Trp Ser Met Tyr Leu Thr Gly His Ile Pro Leu Lys Arg Met
            115                 120                 125 gag cgt cga tcg caa ttg gaa gat ttg aag acg tgc cgc gag atg ctc     432
Glu Arg Arg Ser Gln Leu Glu Asp Leu Lys Thr Cys Arg Glu Met Leu
        130                 135                 140 gcc gac ggt ggt tcg gtt ctt ttc ttc ccg gaa ggg acg aga agc gcc     480
```

```
Ala Asp Gly Gly Ser Val Leu Phe Phe Pro Glu Gly Thr Arg Ser Ala
145                 150                 155                 160 gat ggg aag atg cag gcg ttc aag aag gga gcg ttt agc gtc gcg gct    528
Asp Gly Lys Met Gln Ala Phe Lys Lys Gly Ala Phe Ser Val Ala Ala
                165                 170                 175 aag gaa aat gtc cca gtg gtg ccc gtc acc atc gtc gga gcg cac gag    576
Lys Glu Asn Val Pro Val Val Pro Val Thr Ile Val Gly Ala His Glu
            180                 185                 190 gcc atg gcg agc ggt aag gag tac gcg ctc aac gcg ggt ggg atc aag    624
Ala Met Ala Ser Gly Lys Glu Tyr Ala Leu Asn Ala Gly Gly Ile Lys
        195                 200                 205 gtg atc gtg cac cca ccg att caa tcc acc gac gcc gac gat ctc tgc    672
Val Ile Val His Pro Pro Ile Gln Ser Thr Asp Ala Asp Asp Leu Cys
    210                 215                 220 aag cgt tcc gag gct atc att aag gag agc ctc gtg aac aac tcg tga    720
Lys Arg Ser Glu Ala Ile Ile Lys Glu Ser Leu Val Asn Asn Ser
225                 230                 235
```

<210> SEQ ID NO 2
<211> LENGTH: 239
<212> TYPE: PRT
<213> ORGANISM: Ostreococcus tauri

<400> SEQUENCE: 2

```
Met Leu Val Ala Arg Val Arg Ala Ile Ala Phe Phe Val Thr Ser Phe
1               5                   10                  15

Thr Leu Ala Val Pro Leu Ile Met Ile Met Ala Ile Ile Phe Pro Phe
                20                  25                  30

Gln Tyr Ala Phe Asp Arg Thr Arg Arg Arg Ala Leu Ser Phe Phe Asn
            35                  40                  45

Asp Val Trp Ala Thr Val Ser Thr Gly Leu Phe Phe Pro Ile Glu Val
        50                  55                  60

Val Gly Arg Glu Asn Leu Pro Ser Ala Thr Thr Ala Ala Val Tyr Val
65                  70                  75                  80

Ala Asn His Ala Ser Phe Met Asp Ile Tyr Ser Met Phe His Leu Arg
                85                  90                  95

Arg Pro Phe Lys Phe Val Ser Lys Thr Ser Asn Phe Leu Ile Pro Val
            100                 105                 110

Val Gly Trp Ser Met Tyr Leu Thr Gly His Ile Pro Leu Lys Arg Met
        115                 120                 125

Glu Arg Arg Ser Gln Leu Glu Asp Leu Lys Thr Cys Arg Glu Met Leu
130                 135                 140

Ala Asp Gly Gly Ser Val Leu Phe Phe Pro Glu Gly Thr Arg Ser Ala
145                 150                 155                 160

Asp Gly Lys Met Gln Ala Phe Lys Lys Gly Ala Phe Ser Val Ala Ala
                165                 170                 175

Lys Glu Asn Val Pro Val Val Pro Val Thr Ile Val Gly Ala His Glu
            180                 185                 190

Ala Met Ala Ser Gly Lys Glu Tyr Ala Leu Asn Ala Gly Gly Ile Lys
        195                 200                 205

Val Ile Val His Pro Pro Ile Gln Ser Thr Asp Ala Asp Asp Leu Cys
    210                 215                 220

Lys Arg Ser Glu Ala Ile Ile Lys Glu Ser Leu Val Asn Asn Ser
225                 230                 235
```

<210> SEQ ID NO 3
<211> LENGTH: 702

<212> TYPE: DNA
<213> ORGANISM: Mantoniella squamata
<220> FEATURE:
<221> NAME/KEY: CDS
<222> LOCATION: (1)..(702)

<400> SEQUENCE: 3

```
atg tct ttt tac ctc gtc acc ttc acc ctc gcc tta ccc ctc ttc gcc      48
Met Ser Phe Tyr Leu Val Thr Phe Thr Leu Ala Leu Pro Leu Phe Ala
1               5                   10                  15 gtc atg ctc att ttg ttc ccc ttc acc tac ctc acc gac aag tac cgc      96
Val Met Leu Ile Leu Phe Pro Phe Thr Tyr Leu Thr Asp Lys Tyr Arg
            20                  25                  30 cgc tac gcc ctc agc ttc gtc aac gac gtg tgg gca tgc gtc agc acg     144
Arg Tyr Ala Leu Ser Phe Val Asn Asp Val Trp Ala Cys Val Ser Thr
        35                  40                  45 tgg ttc ttc ttt cct gtc gag gtg att gga aaa gag aac atc cct ccg     192
Trp Phe Phe Phe Pro Val Glu Val Ile Gly Lys Glu Asn Ile Pro Pro
    50                  55                  60 gtc aca aca ccc gca gtg tac gtg gcc aac cac gcg agt tac ctg gac     240
Val Thr Thr Pro Ala Val Tyr Val Ala Asn His Ala Ser Tyr Leu Asp
65                  70                  75                  80 atc tac tcg ctg ttc cac ctc cgc agg ccc ttc aag ttc atc tcg aag     288
Ile Tyr Ser Leu Phe His Leu Arg Arg Pro Phe Lys Phe Ile Ser Lys
                85                  90                  95 gtg tcc aac ttc atc atc ccc atc atc ggg tgg tcc atg tac atg acg     336
Val Ser Asn Phe Ile Ile Pro Ile Ile Gly Trp Ser Met Tyr Met Thr
            100                 105                 110 ggg cac atc gcg ctc aag cgc acg gat cgc aag agc cag atg aaa acc     384
Gly His Ile Ala Leu Lys Arg Thr Asp Arg Lys Ser Gln Met Lys Thr
        115                 120                 125 ttg aag gat tgc cgc gag ttg ttg cag aag aac tgc tcg gtg ctt ttc     432
Leu Lys Asp Cys Arg Glu Leu Leu Gln Lys Asn Cys Ser Val Leu Phe
    130                 135                 140 ttc ccc gaa ggg acg cga agc gtg gac ggc acc atg gcg gag ttc aag     480
Phe Pro Glu Gly Thr Arg Ser Val Asp Gly Thr Met Ala Glu Phe Lys
145                 150                 155                 160 aag ggc gcc ttc agc gtc gcg gcc aag gag aag gcg ctg gtc gtg ccc     528
Lys Gly Ala Phe Ser Val Ala Ala Lys Glu Lys Ala Leu Val Val Pro
                165                 170                 175 atc acg ctc gtg ggc acg tcg gcg agg atg aag aac ggg aag gag tgg     576
Ile Thr Leu Val Gly Thr Ser Ala Arg Met Lys Asn Gly Lys Glu Trp
            180                 185                 190 atg ctg cgc agc ggg ggc atc aag gta gtg gtg cac ccg ccc att cag     624
Met Leu Arg Ser Gly Gly Ile Lys Val Val Val His Pro Pro Ile Gln
        195                 200                 205 agc aaa ggc gac gac gcc caa gag ctc tgc gat gag agc tac aaa acc     672
Ser Lys Gly Asp Asp Ala Gln Glu Leu Cys Asp Glu Ser Tyr Lys Thr
    210                 215                 220 atc aag gag agc ctt gtc aag tac tcg tga                             702
Ile Lys Glu Ser Leu Val Lys Tyr Ser
225                 230
```

<210> SEQ ID NO 4
<211> LENGTH: 233
<212> TYPE: PRT
<213> ORGANISM: Mantoniella squamata

<400> SEQUENCE: 4

```
Met Ser Phe Tyr Leu Val Thr Phe Thr Leu Ala Leu Pro Leu Phe Ala
1               5                   10                  15
```

```
Val Met Leu Ile Leu Phe Pro Phe Thr Tyr Leu Thr Asp Lys Tyr Arg
            20                  25                  30

Arg Tyr Ala Leu Ser Phe Val Asn Asp Val Trp Ala Cys Val Ser Thr
        35                  40                  45

Trp Phe Phe Pro Val Glu Val Ile Gly Lys Glu Asn Ile Pro Pro
50                  55                  60

Val Thr Thr Pro Ala Val Tyr Val Ala Asn His Ala Ser Tyr Leu Asp
65                  70                  75                  80

Ile Tyr Ser Leu Phe His Leu Arg Arg Pro Phe Lys Phe Ile Ser Lys
                85                  90                  95

Val Ser Asn Phe Ile Ile Pro Ile Ile Gly Trp Ser Met Tyr Met Thr
            100                 105                 110

Gly His Ile Ala Leu Lys Arg Thr Asp Arg Lys Ser Gln Met Lys Thr
        115                 120                 125

Leu Lys Asp Cys Arg Glu Leu Leu Gln Lys Asn Cys Ser Val Leu Phe
130                 135                 140

Phe Pro Glu Gly Thr Arg Ser Val Asp Gly Thr Met Ala Glu Phe Lys
145                 150                 155                 160

Lys Gly Ala Phe Ser Val Ala Ala Lys Glu Lys Ala Leu Val Val Pro
                165                 170                 175

Ile Thr Leu Val Gly Thr Ser Ala Arg Met Lys Asn Gly Lys Glu Trp
            180                 185                 190

Met Leu Arg Ser Gly Gly Ile Lys Val Val His Pro Pro Ile Gln
        195                 200                 205

Ser Lys Gly Asp Asp Ala Gln Glu Leu Cys Asp Glu Ser Tyr Lys Thr
210                 215                 220

Ile Lys Glu Ser Leu Val Lys Tyr Ser
225                 230

<210> SEQ ID NO 5
<211> LENGTH: 819
<212> TYPE: DNA
<213> ORGANISM: Mantoniella squamata
<220> FEATURE:
<221> NAME/KEY: CDS
<222> LOCATION: (1)..(819)

<400> SEQUENCE: 5 atg tcg agg tcg acg gta tcg ata agc ttg att agg tgc cag agg acg     48
Met Ser Arg Ser Thr Val Ser Ile Ser Leu Ile Arg Cys Gln Arg Thr
1               5                   10                  15 aga caa ggg gtg tcg tct cag ggc gag gag gat ggc gac aaa ttc tca     96
Arg Gln Gly Val Ser Ser Gln Gly Glu Glu Asp Gly Asp Lys Phe Ser
            20                  25                  30 ctc acc gcc gtc gtc cgc gcc atg tct ttt tac ctc gtc acc ttc acc    144
Leu Thr Ala Val Val Arg Ala Met Ser Phe Tyr Leu Val Thr Phe Thr
        35                  40                  45 ctc gcc tta ccc ctc ttc gcc gtc atg ctc att ttg ttc ccc ttc acc    192
Leu Ala Leu Pro Leu Phe Ala Val Met Leu Ile Leu Phe Pro Phe Thr
50                  55                  60 tac ctc acc gac aag tac cgc cgc tac gcc ctc agc ttc gtc aac gac    240
Tyr Leu Thr Asp Lys Tyr Arg Arg Tyr Ala Leu Ser Phe Val Asn Asp
65                  70                  75                  80 gtg tgg gca tgc gtc agc acg tgg ttc ttc ttt cct gtc gag gtg att    288
Val Trp Ala Cys Val Ser Thr Trp Phe Phe Phe Pro Val Glu Val Ile
                85                  90                  95 gga aaa gag aac atc cct ccg gtc aca aca ccc gca gtg tac gtg gcc    336
Gly Lys Glu Asn Ile Pro Pro Val Thr Thr Pro Ala Val Tyr Val Ala
```

```
aac cac gcg agt tac ctg gac atc tac tcg ctg ttc cac ctc cgc agg       384
Asn His Ala Ser Tyr Leu Asp Ile Tyr Ser Leu Phe His Leu Arg Arg
            115                 120                 125 ccc ttc aag ttc atc tcg aag gtg tcc aac ttc atc atc ccc atc atc       432
Pro Phe Lys Phe Ile Ser Lys Val Ser Asn Phe Ile Ile Pro Ile Ile
130                 135                 140 ggg tgg tcc atg tac atg acg ggg cac atc gcg ctc aag cgc acg gat       480
Gly Trp Ser Met Tyr Met Thr Gly His Ile Ala Leu Lys Arg Thr Asp
145                 150                 155                 160 cgc aag agc cag atg aaa acc ttg aag gat tgc cgc gag ttg ttg cag       528
Arg Lys Ser Gln Met Lys Thr Leu Lys Asp Cys Arg Glu Leu Leu Gln
            165                 170                 175 aag aac tgc tcg gtg ctt ttc ttc ccc gag ggg acg cga agc gtg gac       576
Lys Asn Cys Ser Val Leu Phe Phe Pro Glu Gly Thr Arg Ser Val Asp
            180                 185                 190 ggc acc atg gcg gag ttc aag aag ggc gcc ttc agc gtc gcg gcc aag       624
Gly Thr Met Ala Glu Phe Lys Lys Gly Ala Phe Ser Val Ala Ala Lys
            195                 200                 205 gag aag gcg ctg gtc gtg ccc atc acg ctc gtg ggc acg tcg gcg agg       672
Glu Lys Ala Leu Val Val Pro Ile Thr Leu Val Gly Thr Ser Ala Arg
    210                 215                 220 atg aag aac ggg aag gag tgg atg ctg cgc agc ggg ggc atc aag gta       720
Met Lys Asn Gly Lys Glu Trp Met Leu Arg Ser Gly Gly Ile Lys Val
225                 230                 235                 240 gtg gtg cac ccg ccc att cag agc aaa ggc gac gac gcc caa gag ctc       768
Val Val His Pro Pro Ile Gln Ser Lys Gly Asp Asp Ala Gln Glu Leu
                245                 250                 255 tgc gat gag agc tac aaa acc atc aag gag agc ctt gtc aag tac tcg       816
Cys Asp Glu Ser Tyr Lys Thr Ile Lys Glu Ser Leu Val Lys Tyr Ser
            260                 265                 270 tga                                                                    819

<210> SEQ ID NO 6
<211> LENGTH: 272
<212> TYPE: PRT
<213> ORGANISM: Mantoniella squamata

<400> SEQUENCE: 6

Met Ser Arg Ser Thr Val Ser Ile Ser Leu Ile Arg Cys Gln Arg Thr
1               5                   10                  15

Arg Gln Gly Val Ser Ser Gln Gly Glu Glu Asp Gly Asp Lys Phe Ser
            20                  25                  30

Leu Thr Ala Val Val Arg Ala Met Ser Phe Tyr Leu Val Thr Phe Thr
        35                  40                  45

Leu Ala Leu Pro Leu Phe Ala Val Met Leu Ile Leu Phe Pro Phe Thr
    50                  55                  60

Tyr Leu Thr Asp Lys Tyr Arg Arg Tyr Ala Leu Ser Phe Val Asn Asp
65                  70                  75                  80

Val Trp Ala Cys Val Ser Thr Trp Phe Phe Pro Val Glu Val Ile
                85                  90                  95

Gly Lys Glu Asn Ile Pro Pro Val Thr Thr Pro Ala Val Tyr Val Ala
            100                 105                 110

Asn His Ala Ser Tyr Leu Asp Ile Tyr Ser Leu Phe His Leu Arg Arg
        115                 120                 125

Pro Phe Lys Phe Ile Ser Lys Val Ser Asn Phe Ile Ile Pro Ile Ile
    130                 135                 140
```

```
Gly Trp Ser Met Tyr Met Thr Gly His Ile Ala Leu Lys Arg Thr Asp
145                 150                 155                 160

Arg Lys Ser Gln Met Lys Thr Leu Lys Asp Cys Arg Glu Leu Leu Gln
            165                 170                 175

Lys Asn Cys Ser Val Leu Phe Phe Pro Glu Gly Thr Arg Ser Val Asp
        180                 185                 190

Gly Thr Met Ala Glu Phe Lys Lys Gly Ala Phe Ser Val Ala Ala Lys
    195                 200                 205

Glu Lys Ala Leu Val Val Pro Ile Thr Leu Val Gly Thr Ser Ala Arg
210                 215                 220

Met Lys Asn Gly Lys Glu Trp Met Leu Arg Ser Gly Gly Ile Lys Val
225                 230                 235                 240

Val Val His Pro Pro Ile Gln Ser Lys Gly Asp Asp Ala Gln Glu Leu
            245                 250                 255

Cys Asp Glu Ser Tyr Lys Thr Ile Lys Glu Ser Leu Val Lys Tyr Ser
        260                 265                 270

<210> SEQ ID NO 7
<211> LENGTH: 6613
<212> TYPE: DNA
<213> ORGANISM: Unknown
<220> FEATURE:
<223> OTHER INFORMATION: yeast expression vector
<220> FEATURE:
<221> NAME/KEY: misc_feature
<223> OTHER INFORMATION: pYES2-Ot_LPCAT

<400> SEQUENCE: 7
acggattaga agccgccgag cgggtgacag ccctccgaag gaagactctc ctccgtgcgt      60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240 ttagttttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctcgccc ttatgctggt cgcgcgcgtc cgagcgatcg    540
ccttcttcgt cacctcgttc acgctcgcgg tgccgctcat catgatcatg gcgatcatat    600
tcccgtttca gtacgcgttc gatcgaacgc gaaggcgggc gctgagtttc ttcaacgacg    660
tctgggcgac ggtgtccact gggttgttct ttccgattga agtcgtcgga cgggagaatt    720
tgccgagcgc gacgacggcg gcggtgtacg tcgcgaatca cgcgtcgttc atggatattt    780
attccatgtt tcacctgcga cgcccgttca gtttgtgtc caagacgagc aacttttttga    840 tccccgtcgt cgggtggtcg atgtatctca cgggacacat ccctctgaag cgcatggagc    900
gtcgatcgca attggaagat ttgaagacgt gccgcgagat gctcgccgac ggtggttcgg    960
ttcttttctt cccggaaggg acgagaagcg ccgatgggaa gatgcaggcg ttcaagaagg   1020
gagcgtttag cgtcgcggct aaggaaaatg tcccagtggt gcccgtcacc atcgtcggag   1080
cgcacgaggc catggcgagc ggtaaggagt acgcgctcaa cgcgggtggg atcaaggtga   1140
tcgtgcaccc accgattcaa tccaccgacg ccgacgatct ctgcaagcgt tccgaggcta   1200
tcattaagga gagcctcgtg aacaactcgt gactcgagta agggcgagct tcgaggtcac   1260
```

```
ccattcgaag gtaagcctat ccctaaccct ctcctcggtc tcgattctac gcgtaccggt    1320
catcatcacc atcaccattg agtttctaga gggccgcatc atgtaattag ttatgtcacg    1380
cttacattca cgccctcccc ccacatccgc tctaaccgaa aaggaaggag ttagacaacc    1440
tgaagtctag gtccctattt attttttttat agttatgtta gtattaagaa cgttatttat    1500
atttcaaatt tttcttttttt ttctgtacag acgcgtgtac gcatgtaaca ttatactgaa    1560
aaccttgctt gagaaggttt tgggacgctc gaaggcttta atttgcaagc tgcggccctg    1620
cattaatgaa tcggccaacg cgcggggaga ggcggtttgc gtattgggcg ctcttccgct    1680
tcctcgctca ctgactcgct gcgctcggtc gttcggctgc ggcgagcggt atcagctcac    1740
tcaaaggcgg taatacggtt atccacagaa tcaggggata acgcaggaaa gaacatgtga    1800
gcaaaaggcc agcaaaagcc caggaaccgt aaaaaggccg cgttgctggc gttttttccat    1860 aggctccgcc cccctgacga gcatcacaaa aatcgacgct caagtcagag gtggcgaaac    1920
ccgacaggac tataaagata ccaggcgttt ccccctggaa gctccctcgt gcgctctcct    1980
gttccgaccc tgccgcttac cggatacctg tccgcctttc tcccttcggg aagcgtggcg    2040
ctttctcata gctcacgctg taggtatctc agttcggtgt aggtcgttcg ctccaagctg    2100
ggctgtgtgc acgaaccccc cgttcagccc gaccgctgcg ccttatccgg taactatcgt    2160
cttgagtcca acccggtaag acacgactta tcgccactgg cagcagccac tggtaacagg    2220
attagcagag cgaggtatgt aggcggtgct acagagttct tgaagtggtg gcctaactac    2280
ggctacacta gaaggacagt atttggtatc tgcgctctgc tgaagccagt taccttcgga    2340
aaaagagttg gtagctcttg atccggcaaa caaaccaccg ctggtagcgg tggtttttttt    2400 gtttgcaagc agcagattac gcgcagaaaa aaaggatctc aagaagatcc tttgatcttt    2460
tctacggggt ctgacgctca gtggaacgaa aactcacgtt aagggatttt ggtcatgaga    2520
ttatcaaaaa ggatcttcac ctagatcctt ttaaattaaa aatgaagttt taaatcaatc    2580
taaagtatat atgagtaaac ttggtctgac agttaccaat gcttaatcag tgaggcacct    2640
atctcagcga tctgtctatt tcgttcatcc atagttgcct gactccccgt cgtgtagata    2700
actacgatac gggagcgctt accatctggc cccagtgctg caatgatacc gcgagaccca    2760
cgctcaccgg ctccagattt atcagcaata aaccagccag ccggaagggc cgagcgcaga    2820
agtggtcctg caactttatc cgcctccatt cagtctatta attgttgccg ggaagctaga    2880
gtaagtagtt cgccagttaa tagtttcgc aacgttgttg gcattgctac aggcatcgtg    2940
gtgtcactct cgtcgtttgg tatggcttca ttcagctccg gttcccaacg atcaaggcga    3000
gttacatgat cccccatgtt gtgcaaaaaa gcggttagct ccttcggtcc tccgatcgtt    3060
gtcagaagta agttggccgc agtgttatca ctcatggtta tggcagcact gcataattct    3120
cttactgtca tgccatccgt aagatgcttt tctgtgactg gtgagtactc aaccaagtca    3180
ttctgagaat agtgtatgcg cgaccgagt tgctcttgcc cggcgtcaat acgggataat    3240
agtgtatcac atagcagaac tttaaaagtg ctcatcattg gaaaacgttc ttcggggcga    3300
aaactctcaa ggatcttacc gctgttgaga tccagttcga tgtaacccac tcgtgcaccc    3360
aactgatctt cagcatcttt tactttcacc agcgtttctg ggtgagcaaa aacaggaagg    3420
caaaatgccg caaaaaaggg aataagggcg acacggaaat gttgaatact catactcttc    3480
ctttttcaat gggtaataac tgatataatt aaattgaagc tctaatttgt gagtttagta    3540
tacatgcatt tacttataat acagtttttt agttttgctg gccgcatctt ctcaaatatg    3600
cttcccagcc tgcttttctg taacgttcac cctctacctt agcatccctt cccttttgcaa    3660
```

```
atagtcctct tccaacaata ataatgtcag atcctgtaga gaccacatca tccacggttc  3720
tatactgttg acccaatgcg tctcccttgt catctaaacc cacaccgggt gtcataatca  3780
accaatcgta accttcatct cttccaccca tgtctctttg agcaataaag ccgataacaa  3840
aatctttgtc gctcttcgca atgtcaacag taccccttagt atattctcca gtagataggg  3900
agcccttgca tgacaattct gctaacatca aaaggcctct aggttccttt gttacttctt  3960
ctgccgcctg cttcaaaccg ctaacaatac ctgggcccac cacaccgtgt gcattcgtaa  4020
tgtctgccca ttctgctatt ctgtatacac ccgcagagta ctgcaatttg actgtattac  4080
caatgtcagc aaattttctg tcttcgaaga gtaaaaaatt gtacttggcg ataatgcct   4140 ttagcggctt aactgtgccc tccatggaaa aatcagtcaa gatatccaca tgtgttttta  4200
gtaaacaaat tttgggacct aatgcttcaa ctaactccag taattccttg gtggtacgaa  4260
catccaatga agcacacaag tttgtttgct tttcgtgcat gatattaaat agcttggcag  4320
caacaggact aggatgagta gcagcacgtt ccttatatgt agctttcgac atgatttatc  4380
ttcgtttcct gcaggttttt gttctgtgca gttgggttaa gaatactggg caatttcatg  4440
tttcttcaac actacatatg cgtatatata ccaatctaag tctgtgctcc ttccttcgtt  4500
cttccttctg ttcggagatt accgaatcaa aaaatttca agaaaccga aatcaaaaaa    4560 aagaataaaa aaaaaatgat gaattgaatt gaaaagctag cttatcgatg ataagctgtc  4620
aaagatgaga attaattcca cggactatag actatactag atactccgtc tactgtacga  4680
tacacttccg ctcaggtcct tgtcctttaa cgaggcctta ccactctttt gttactctat  4740
tgatccagct cagcaaaggc agtgtgatct aagattctat cttcgcgatg tagtaaaact  4800
agctagaccg agaaagagac tagaaatgca aaaggcactt ctacaatggc tgccatcatt  4860
attatccgat gtgacgctgc agcttctcaa tgatattcga atacgctttg aggagataca  4920
gcctaatatc cgacaaactg ttttacagat ttacgatcgt acttgttacc catcattgaa  4980
ttttgaacat ccgaacctgg gagttttccc tgaaacagat agtatatttg aacctgtata  5040
ataatatata gtctagcgct ttacggaaga caatgtatgt atttcggttc ctggagaaac  5100
tattgcatct attgcatagg taatcttgca cgtcgcatcc ccggttcatt ttctgcgttt  5160
ccatcttgca cttcaatagc atatctttgt taacgaagca tctgtgcttc attttgtaga  5220
acaaaaatgc aacgcgagag cgctaatttt tcaaacaaag aatctgagct gcattttac   5280 agaacagaaa tgcaacgcga aagcgctatt ttaccaacga agaatctgtg cttcattttt  5340
gtaaaacaaa aatgcaacgc gacgagagcg ctaattttc aaacaaagaa tctgagctgc  5400 attttacag aacagaaatg caacgcgaga gcgctatttt accaacaaag aatctatact  5460
tcttttttgt tctacaaaaa tgcatcccga gagcgctatt tttctaacaa agcatcttag  5520
attacttttt ttctccttg tgcgctctat aatgcagtct cttgataact ttttgcactg  5580
taggtccgtt aaggttagaa gaaggctact ttggtgtcta ttttctcttc cataaaaaaa  5640
gcctgactcc acttcccgcg tttactgatt actagcgaag ctgcgggtgc attttttcaa  5700
gataaaggca tccccgatta tattctatac cgatgtggat tgcgcatact tgtgaacag   5760 aaagtgatag cgttgatgat tcttcattgg tcagaaaatt atgaacggtt tcttctattt  5820
tgtctctata tactacgtat aggaaatgtt tacattttcg tattgttttc gattcactct  5880
atgaatagtt cttactacaa ttttttttgtc taaagagtaa tactagagat aaacataaaa  5940
aatgtagagg tcgagtttag atgcaagttc aaggagcgaa aggtggatgg gtaggttata  6000
```

```
tagggatata gcacagagat atatagcaaa gagatacttt tgagcaatgt ttgtggaagc    6060
ggtattcgca atgggaagct ccaccccggt tgataatcag aaaagcccca aaaacaggaa    6120
gattgtataa gcaaatattt aaattgtaaa cgttaatatt ttgttaaaat tcgcgttaaa    6180
tttttgttaa atcagctcat tttttaacga atagcccgaa atcggcaaaa tcccttataa    6240
atcaaaagaa tagaccgaga tagggttgag tgttgttcca gtttccaaca agagtccact    6300
attaaagaac gtggactcca acgtcaaagg gcgaaaaagg gtctatcagg gcgatggccc    6360
actacgtgaa ccatcaccct aatcaagttt ttggggtcg aggtgccgta aagcagtaaa     6420
tcggaagggt aaacgatgc ccccatttag agcttgacgg ggaaagccgg cgaacgtggc     6480
gagaaaggaa gggaagaaag cgaaaggagc ggggggctagg gcggtgggaa gtgtaggggt    6540
cacgctgggc gtaaccacca cacccgccgc gcttaatggg gcgctacagg gcgcgtgggg    6600
atgatccact agt                                                      6613

<210> SEQ ID NO 8
<211> LENGTH: 6602
<212> TYPE: DNA
<213> ORGANISM: Unknown
<220> FEATURE:
<223> OTHER INFORMATION: yeast expression vector
<220> FEATURE:
<221> NAME/KEY: misc_feature
<223> OTHER INFORMATION: pYES2-MA_112-LPCAT

<400> SEQUENCE: 8
acggattaga agccgccgag cgggtgacag ccctccgaag gaagactctc ctccgtgcgt      60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agcctatttt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctcgccc ttaggatcca tgtcttttta cctcgtcacc    540
ttcaccctcg ccttacccct cttcgccgtc atgctcattt tgttccccct cacctacctc    600
accgacaagt accgccgcta cgccctcagc ttcgtcaacg acgtgtgggc atgcgtcagc    660
acgtggttct tctttcctgt cgaggtgatt ggaaaagaga acatccctcc ggtcacaaca    720
cccgcagtgt acgtggccaa ccacgcgagt tacctggaca tctactcgct gttccacctc    780
cgcaggccct tcaagttcat ctcgaaggtg tccaacttca tcatccccat catcgggtgg    840
tccatgtaca tgacggggca catcgcgctc aagcgcacgg atcgcaagag ccagatgaaa    900
accttgaagg attgccgcga gttgttgcag aagaactgct cggtgctttt cttccccgaa    960
gggacgcgaa gcgtggacgg caccatggcg gagttcaaga agggcgcctt cagcgtcgcg    1020
gccaaggaga aggcgctggt cgtgcccatc acgctcgtgg gcacgtcggc gaggatgaag    1080
aacgggaagg agtggatgct gcgcagcggg ggcatcaagg tagtggtgca cccgcccatt    1140
cagagcaaag gcgacgacgc ccaagagctc tgcgatgaga gctacaaaac catcaaggag    1200
agccttgtca gtactcgtg actcgagtaa gggcgagctt cgaggtcacc cattcgaagg    1260
taagcctatc cctaaccctc tcctcggtct cgattctacg cgtaccggtc atcatcacca    1320
```

-continued

```
tcaccattga gtttctagag ggccgcatca tgtaattagt tatgtcacgc ttacattcac   1380
gccctccccc cacatccgct ctaaccgaaa aggaaggagt tagacaacct gaagtctagg   1440
tccctattta tttttttata gttatgttag tattaagaac gttatttata tttcaaattt   1500 ttctttttt tctgtacaga cgcgtgtacg catgtaacat tatactgaaa accttgcttg   1560
agaaggtttt gggacgctcg aaggctttaa tttgcaagct gcggccctgc attaatgaat   1620
cggccaacgc gcggggagag gcggtttgcg tattgggcgc tcttccgctt cctcgctcac   1680
tgactcgctg cgctcggtcg ttcggctgcg gcgagcggta tcagctcact caaaggcggt   1740
aatacggtta tccacagaat cagggggataa cgcaggaaag aacatgtgag caaaaggcca   1800
gcaaaagccc aggaaccgta aaaaggccgc gttgctggcg ttttccata ggctccgccc   1860 ccctgacgag catcacaaaa atcgacgctc aagtcagagg tggcgaaacc cgacaggact   1920
ataaagatac caggcgtttc ccctggaag ctccctcgtg cgctctcctg ttccgaccct   1980
gccgcttacc ggatacctgt ccgcctttct cccttcggga agcgtggcgc tttctcatag   2040
ctcacgctgt aggtatctca gttcggtgta ggtcgttcgc tccaagctgg gctgtgtgca   2100
cgaacccccc gttcagcccg accgctgcgc cttatccggt aactatcgtc ttgagtccaa   2160
cccggtaaga cacgacttat cgccactggc agcagccact ggtaacagga ttagcagagc   2220
gaggtatgta ggcggtgcta cagagttctt gaagtggtgg cctaactacg gctacactag   2280
aaggacagta tttggtatct gcgctctgct gaagccagtt accttcggaa aaagagttgg   2340
tagctcttga tccggcaaac aaaccaccgc tggtagcggt ggtttttttg tttgcaagca   2400
gcagattacg cgcagaaaaa aaggatctca agaagatcct ttgatctttt ctacggggtc   2460
tgacgctcag tggaacgaaa actcacgtta agggattttg gtcatgagat tatcaaaaag   2520
gatcttcacc tagatccttt taaattaaaa atgaagtttt aaatcaatct aaagtatata   2580
tgagtaaact tggtctgaca gttaccaatg cttaatcagt gaggcaccta tctcagcgat   2640
ctgtctattt cgttcatcca tagttgcctg actccccgtc gtgtagataa ctacgatacg   2700
ggagcgctta ccatctggcc ccagtgctgc aatgataccg cgagacccac gctcaccggc   2760
tccagattta tcagcaataa accagccagc cggaagggcc gagcgcagaa gtggtcctgc   2820
aactttatcc gcctccattc agtctattaa ttgttgccgg gaagctagag taagtagttc   2880
gccagttaat agtttgcgca acgttgttgg cattgctaca ggcatcgtgg tgtcactctc   2940
gtcgtttggt atggcttcat tcagctccgg ttcccaacga tcaaggcgag ttacatgatc   3000
ccccatgttg tgcaaaaaag cggttagctc cttcggtcct ccgatcgttg tcagaagtaa   3060
gttggccgca gtgttatcac tcatggttat ggcagcactg cataattctc ttactgtcat   3120
gccatccgta agatgctttt ctgtgactgg tgagtactca accaagtcat tctgagaata   3180
gtgtatgcgg cgaccgagtt gctcttgccc ggcgtcaata cgggataata gtgtatcaca   3240
tagcagaact ttaaaagtgc tcatcattgg aaaacgttct cggggcgaa aactctcaag   3300 gatcttaccg ctgttgagat ccagttcgat gtaacccact cgtgcaccca actgatcttc   3360
agcatctttt actttcacca gcgtttctgg gtgagcaaaa acaggaaggc aaaatgccgc   3420
aaaaaaggga ataagggcga cacggaaatg ttgaatactc atactcttcc ttttcaatg    3480 ggtaataact gatataatta aattgaagct ctaatttgtg agtttagtat acatgcattt   3540
acttataata cagttttta gttttgctgg ccgcatcttc tcaaatatgc ttcccagcct   3600
gcttttctgt aacgttcacc ctctacctta gcatccttc cctttgcaaa tagtcctctt   3660
ccaacaataa taatgtcaga tcctgtagag accacatcat ccacggttct atactgttga   3720
```

```
cccaatgcgt ctcccttgtc atctaaaccc acaccgggtg tcataatcaa ccaatcgtaa   3780
ccttcatctc ttccacccat gtctctttga gcaataaagc cgataacaaa atctttgtcg   3840
ctcttcgcaa tgtcaacagt acccttagta tattctccag tagataggga gcccttgcat   3900
gacaattctg ctaacatcaa aaggcctcta ggttcctttg ttacttcttc tgccgcctgc   3960
ttcaaaccgc taacaatacc tgggcccacc acaccgtgtg cattcgtaat gtctgcccat   4020
tctgctattc tgtatacacc cgcagagtac tgcaatttga ctgtattacc aatgtcagca   4080
aattttctgt cttcgaagag taaaaaattg tacttggcgg ataatgcctt tagcggctta   4140
actgtgccct ccatggaaaa atcagtcaag atatccacat gtgtttttag taaacaaatt   4200
ttgggaccta atgcttcaac taactccagt aattccttgg tggtacgaac atccaatgaa   4260
gcacacaagt ttgtttgctt ttcgtgcatg atattaaata gcttggcagc aacaggacta   4320
ggatgagtag cagcacgttc cttatatgta gctttcgaca tgatttatct tcgtttcctg   4380 caggttttg ttctgtgcag ttgggttaag aatactgggc aatttcatgt tcttcaaca    4440 ctacatatgc gtatatatac caatctaagt ctgtgctcct tccttcgttc ttccttctgt   4500
tcggagatta ccgaatcaaa aaatttcaa agaaaccgaa atcaaaaaaa agaataaaaa    4560
aaaaatgatg aattgaattg aaaagctagc ttatcgatga taagctgtca agatgagaa    4620 ttaattccac ggactataga ctatactaga tactccgtct actgtacgat acacttccgc   4680
tcaggtcctt gtcctttaac gaggccttac cactcttttg ttactctatt gatccagctc   4740
agcaaaggca gtgtgatcta agattctatc ttcgcgatgt agtaaaacta gctagaccga   4800
gaaagagact agaaatgcaa aaggcacttc tacaatggct gccatcatta ttatccgatg   4860
tgacgctgca gcttctcaat gatattcgaa tacgctttga ggagatacag cctaatatcc   4920
gacaaactgt tttacagatt tacgatcgta cttgttaccc atcattgaat tttgaacatc   4980
cgaacctggg agttttccct gaaacagata gtatatttga acctgtataa taatatatag   5040
tctagcgctt tacggaagac aatgtatgta tttcggttcc tggagaaact attgcatcta   5100
ttgcataggt aatcttgcac gtcgcatccc cggttcattt tctgcgtttc catcttgcac   5160
ttcaatagca tatctttgtt aacgaagcat ctgtgcttca ttttgtagaa caaaaatgca   5220
acgcgagagc gctaattttt caaacaaaga atctgagctg cattttaca gaacagaaat    5280 gcaacgcgaa agcgctattt taccaacgaa gaatctgtgc ttcattttg taaaacaaaa    5340 atgcaacgcg acgagagcgc taatttttca aacaaagaat ctgagctgca ttttacaga   5400 acagaaatgc aacgcgagag cgctatttta ccaacaaaga atctatactt cttttttgtt   5460
ctacaaaaat gcatcccgag agcgctattt tctaacaaa gcatcttaga ttactttttt    5520
tctcctttgt gcgctctata atgcagtctc ttgataactt tttgcactgt aggtccgtta   5580
aggttagaag aaggctactt tggtgtctat tttctcttcc ataaaaaaag cctgactcca   5640
cttcccgcgt ttactgatta ctagcgaagc tgcgggtgca ttttttcaag ataaaggcat   5700
ccccgattat attctatacc gatgtggatt gcgcatactt tgtgaacaga agtgatagc    5760 gttgatgatt cttcattggt cagaaaatta tgaacggttt cttctatttt gtctctatat   5820
actacgtata ggaaatgttt acattttcgt attgttttcg attcactcta tgaatagttc   5880
ttactacaat ttttttgtct aaagagtaat actagagata aacataaaaa atgtagaggt   5940
cgagtttaga tgcaagttca aggagcgaaa ggtggatggg taggttatat agggatatag   6000
cacagagata tatagcaaag agatactttt gagcaatgtt tgtggaagcg gtattcgcaa   6060
```

-continued

| | |
|---|---|
| tgggaagctc acccccggtt gataatcaga aaagccccaa aaacaggaag attgtataag | 6120 |
| caaatatttta aattgtaaac gttaatattt tgttaaaatt cgcgttaaat ttttgttaaa | 6180 |
| tcagctcatt ttttaacgaa tagcccgaaa tcggcaaaat cccttataaa tcaaaagaat | 6240 |
| agaccgagat agggttgagt gttgttccag tttccaacaa gagtccacta ttaaagaacg | 6300 |
| tggactccaa cgtcaaaggg cgaaaaaggg tctatcaggg cgatggccca ctacgtgaac | 6360 |
| catcacccta atcaagtttt tgggggtcga ggtgccgtaa agcagtaaat cggaagggta | 6420 |
| aacggatgcc cccatttaga gcttgacggg gaaagccggc gaacgtggcg agaaaggaag | 6480 |
| ggaagaaagc gaaaggagcg ggggctaggg cggtgggaag tgtaggggtc acgctgggcg | 6540 |
| taaccaccac acccgccgcg cttaatgggg cgctacaggg cgcgtgggga tgatccacta | 6600 |
| gt | 6602 |

<210> SEQ ID NO 9
<211> LENGTH: 6712
<212> TYPE: DNA
<213> ORGANISM: Unknown
<220> FEATURE:
<223> OTHER INFORMATION: yeast expression vector
<220> FEATURE:
<221> NAME/KEY: misc_feature
<223> OTHER INFORMATION: pYES2-MA_118-LPCAT

<400> SEQUENCE: 9

| | |
|---|---|
| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagcttttta tggttatgaa gaggaaaaat tggcagtaac | 180 |
| ctggccccac aaaccttcaa atgaacgaat caaattaaca accataggat gataatgcga | 240 |
| ttagtttttt agccttattt ctggggtaat taatcagcga agcgatgatt tttgatctat | 300 |
| taacagatat ataaatgcaa aaactgcata accactttaa ctaatacttt caacattttc | 360 |
| ggtttgtatt acttcttatt caaatgtaat aaaagtatca acaaaaaatt gttaatatac | 420 |
| ctctatactt taacgtcaag gagaaaaaac cccggatcgg actactagca gctgtaatac | 480 |
| gactcactat agggaatatt aagctcgccc ttatgtcgag gtcgacggta tcgataagct | 540 |
| tgattaggtg ccagaggacg agacaagggg tgtcgtctca gggcgaggag gatggcgaca | 600 |
| aattctcact caccgccgtc gtccgcgcca tgtctttta cctcgtcacc ttcaccctcg | 660 |
| ccttacccct cttcgccgtc atgctcattt tgttcccctt cacctacctc accgacaagt | 720 |
| accgccgcta cgccctcagc ttcgtcaacg acgtgtgggc atgcgtcagc acgtggttct | 780 |
| tctttcctgt cgaggtgatt ggaaaagaga acatccctcc ggtcacaaca cccgcagtgt | 840 |
| acgtggccaa ccacgcgagt tacctggaca tctactcgct gttccacctc cgcaggccct | 900 |
| tcaagttcat ctcgaaggtg tccaacttca tcatccccat catcgggtgg tccatgtaca | 960 |
| tgacggggca catcgcgctc aagcgcacgg atcgcaagag ccagatgaaa accttgaagg | 1020 |
| attgccgcga gttgttgcag aagaactgct cggtgctttt cttccccgag ggacgcgaa | 1080 |
| gcgtggacgg caccatggcg gagttcaaga agggcgcctt cagcgtcgcg gccaaggaga | 1140 |
| aggcgctggt cgtgcccatc acgctcgtgg gcacgtcggc gaggatgaag aacgggaagg | 1200 |
| agtggatgct gcgcagcggg ggcatcaagg tagtggtgca cccgcccatt cagagcaaag | 1260 |
| gcgacgacgc ccaagagctc tgcgatgaga gctacaaaac catcaaggag agccttgtca | 1320 |
| agtactcgtg aatcgagtaa gggcgagctt cgaggtcacc cattcgaagg taagcctatc | 1380 |

```
cctaaccctc tcctcggtct cgattctacg cgtaccggtc atcatcacca tcaccattga  1440
gtttctagag ggccgcatca tgtaattagt tatgtcacgc ttacattcac gccctccccc  1500
cacatccgct ctaaccgaaa aggaaggagt tagacaacct gaagtctagg tccctattta  1560
tttttttata gttatgttag tattaagaac gttatttata tttcaaattt ttctttttt  1620 tctgtacaga cgcgtgtacg catgtaacat tatactgaaa accttgcttg agaaggtttt  1680
gggacgctcg aaggctttaa tttgcaagct gcggccctgc attaatgaat cggccaacgc  1740
gcggggagag gcggtttgcg tattgggcgc tcttccgctt cctcgctcac tgactcgctg  1800
cgctcggtcg ttcggctgcg gcgagcggta tcagctcact caaaggcggt aatacggtta  1860
tccacagaat caggggataa cgcaggaaag aacatgtgag caaaaggcca gcaaagccc  1920 aggaaccgta aaaaggccgc gttgctggcg ttttccata ggctccgccc cctgacgag  1980 catcacaaaa atcgacgctc aagtcagagg tggcgaaacc cgacaggact ataaagatac  2040
caggcgtttc ccctggaag ctccctcgtg cgctctcctg ttccgaccct gccgcttacc  2100
ggatacctgt ccgcctttct cccttcggga agcgtggcgc tttctcatag ctcacgctgt  2160
aggtatctca gttcggtgta ggtcgttcgc tccaagctgg gctgtgtgca cgaaccccc  2220 gttcagcccg accgctgcgc cttatccggt aactatcgtc ttgagtccaa cccggtaaga  2280
cacgacttat cgccactggc agcagccact ggtaacagga ttagcagagc gaggtatgta  2340
ggcggtgcta cagagttctt gaagtggtgg cctaactacg gctacactag aaggacagta  2400
tttggtatct gcgctctgct gaagccagtt accttcggaa aaagagttgg tagctcttga  2460
tccggcaaac aaaccaccgc tggtagcggt ggtttttttg tttgcaagca gcagattacg  2520
cgcagaaaaa aaggatctca agaagatcct ttgatctttt ctacgggtc tgacgctcag  2580 tggaacgaaa actcacgtta agggattttg gtcatgagat tatcaaaaag gatcttcacc  2640
tagatccttt taaattaaaa atgaagtttt aaatcaatct aaagtatata tgagtaaact  2700
tggtctgaca gttaccaatg cttaatcagt gaggcaccta tctcagcgat ctgtctattt  2760
cgttcatcca tagttgcctg actccccgtc gtgtagataa ctacgatacg ggagcgctta  2820
ccatctggcc ccagtgctgc aatgataccg cgagacccac gctcaccggc tccagattta  2880
tcagcaataa accagccagc cggaagggcc gagcgcagaa gtggtcctgc aactttatcc  2940
gcctccattc agtctattaa ttgttgccgg gaagctagag taagtagttc gccagttaat  3000
agtttgcgca acgttgttgg cattgctaca ggcatcgtgg tgtcactctc gtcgtttggt  3060
atggcttcat tcagctccgg ttcccaacga tcaaggcgag ttacatgatc ccccatgttg  3120
tgcaaaaaag cggttagctc cttcggtcct ccgatcgttg tcagaagtaa gttggccgca  3180
gtgttatcac tcatggttat ggcagcactg cataattctc ttactgtcat gccatccgta  3240
agatgctttt ctgtgactgg tgagtactca accaagtcat tctgagaata gtgtatgcgg  3300
cgaccgagtt gctcttgccc ggcgtcaata cgggataata gtgtatcaca tagcagaact  3360
ttaaaagtgc tcatcattgg aaaacgttct tcggggcgaa aactctcaag gatcttaccg  3420
ctgttgagat ccagttcgat gtaacccact cgtgcaccca actgatcttc agcatctttt  3480
actttcacca gcgtttctgg gtgagcaaaa acaggaaggc aaaatgccgc aaaaaaggga  3540
ataagggcga cacggaaatg ttgaatactc atactcttcc ttttcaatg ggtaataact  3600 gatataatta aattgaagct ctaatttgtg agtttagtat acatgcattt acttataata  3660
cagtttttta gttttgctgg ccgcatcttc tcaaatatgc ttcccagcct gcttttctgt  3720
aacgttcacc ctctacctta gcatcccttc cctttgcaaa tagtcctctt ccaacaataa  3780
```

```
taatgtcaga tcctgtagag accacatcat ccacggttct atactgttga cccaatgcgt    3840
ctcccttgtc atctaaaccc acaccgggtg tcataatcaa ccaatcgtaa ccttcatctc    3900
ttccacccat gtctctttga gcaataaagc cgataacaaa atctttgtcg ctcttcgcaa    3960
tgtcaacagt acccttagta tattctccag tagataggga gcccttgcat gacaattctg    4020
ctaacatcaa aaggcctcta ggttcctttg ttacttcttc tgccgcctgc ttcaaaccgc    4080
taacaatacc tgggcccacc acaccgtgtg cattcgtaat gtctgcccat tctgctattc    4140
tgtatacacc cgcagagtac tgcaatttga ctgtattacc aatgtcagca aatttttctgt   4200
cttcgaagag taaaaaattg tacttggcgg ataatgcctt tagcggctta actgtgccct    4260
ccatggaaaa atcagtcaag atatccacat gtgtttttag taaacaaatt ttgggaccta    4320
atgcttcaac taactccagt aattccttgg tggtacgaac atccaatgaa gcacacaagt    4380
ttgtttgctt ttcgtgcatg atattaaata gcttggcagc aacaggacta ggatgagtag    4440
cagcacgttc cttatatgta gctttcgaca tgatttatct tcgtttcctg caggttttg     4500
ttctgtgcag ttgggttaag aatactgggc aatttcatgt ttcttcaaca ctacatatgc    4560
gtatatatac caatctaagt ctgtgctcct tccttcgttc ttccttctgt tcggagatta    4620
ccgaatcaaa aaaatttcaa agaaaccgaa atcaaaaaaa agaataaaaa aaaaatgatg    4680
aattgaattg aaaagctagc ttatcgatga taagctgtca aagatgagaa ttaattccac    4740
ggactataga ctatactaga tactccgtct actgtacgat acacttccgc tcaggtcctt    4800
gtcctttaac gaggccttac cactcttttg ttactctatt gatccagctc agcaaaggca    4860
gtgtgatcta agattctatc ttcgcgatgt agtaaaacta gctagaccga gaaagagact    4920
agaaatgcaa aaggcacttc tacaatggct gccatcatta ttatccgatg tgacgctgca    4980
gcttctcaat gatattcgaa tacgctttga ggagatacag cctaatatcc gacaaactgt    5040
tttacagatt tacgatcgta cttgttaccc atcattgaat tttgaacatc cgaacctggg    5100
agttttccct gaaacagata gtatatttga acctgtataa taatatatag tctagcgctt    5160
tacgaaagac aatgtatgta tttcggttcc tggagaaact attgcatcta ttgcataggt    5220
aatcttgcac gtcgcatccc cggttcattt tctgcgtttc catcttgcac ttcaatagca    5280
tatctttgtt aacgaagcat ctgtgcttca ttttgtagaa caaaaatgca acgcgagagc    5340
gctaattttt caaacaaaga atctgagctg cattttaca gaacagaaat gcaacgcgaa     5400
agcgctattt taccaacgaa gaatctgtgc ttcattttg taaacaaaa atgcaacgcg       5460
acgagagcgc taattttttca aacaaagaat ctgagctgca ttttacaga acagaaatgc     5520
aacgcgagag cgctatttta ccaacaaaga atctatactt cttttttgtt ctacaaaaat    5580
gcatcccgag agcgctattt tctaacaaa gcatcttaga ttactttttt tctcctttgt     5640
gcgctctata atgcagtctc ttgataactt tttgcactgt aggtccgtta aggttagaag    5700
aaggctactt tggtgtctat tttctcttcc ataaaaaaag cctgactcca cttcccgcgt    5760
ttactgatta ctagcgaagc tgcgggtgca ttttttcaag ataaaggcat ccccgattat    5820
attctatacc gatgtggatt gcgcatactt tgtgaacaga aagtgatagc gttgatgatt    5880
cttcattggt cagaaaatta tgaacggttt cttctatttt gtctctatat actacgtata    5940
ggaaatgttt acattttcgt attgttttcg attcactcta tgaatagttc ttactacaat    6000
ttttttgtct aaagagtaat actagagata aacataaaaa atgtagaggt cgagtttaga    6060
tgcaagttca aggagcgaaa ggtggatggg taggttatat agggatatag cacagagata    6120
```

-continued

```
tatagcaaag agatactttt gagcaatgtt tgtggaagcg gtattcgcaa tgggaagctc    6180
caccccggtt gataatcaga aaagccccaa aaacaggaag attgtataag caaatattta    6240
aattgtaaac gttaatattt tgttaaaatt cgcgttaaat ttttgttaaa tcagctcatt    6300
ttttaacgaa tagcccgaaa tcggcaaaat cccttataaa tcaaaagaat agaccgagat    6360
agggttgagt gttgttccag tttccaacaa gagtccacta ttaaagaacg tggactccaa    6420
cgtcaaaggg cgaaaaggg tctatcaggg cgatggccca ctacgtgaac catcacccta     6480
atcaagtttt tgggtcga ggtgccgtaa agcagtaaat cggaagggta acggatgcc      6540 cccatttaga gcttgacggg gaaagccggc gaacgtggcg agaaaggaag ggaagaaagc    6600
gaaaggagcg ggggctaggg cggtgggaag tgtagggtc acgctgggcg taaccaccac     6660
acccgccgcg cttaatgggg cgctacaggg cgcgtgggga tgatccacta gt           6712
```

```
<210> SEQ ID NO 10
<211> LENGTH: 23
<212> TYPE: DNA
<213> ORGANISM: Artificial sequence
<220> FEATURE:
<223> OTHER INFORMATION: primer 5'-119-Ot-LPCAT

<400> SEQUENCE: 10
atgctggtcg cgcgcgtccg agc                                             23

<210> SEQ ID NO 11
<211> LENGTH: 27
<212> TYPE: DNA
<213> ORGANISM: Artificial sequence
<220> FEATURE:
<223> OTHER INFORMATION: primer 3'-120-Ot-LPCAT-XhoI

<400> SEQUENCE: 11
actcgagtca cgagttgttc acgaggc                                         27

<210> SEQ ID NO 12
<211> LENGTH: 34
<212> TYPE: DNA
<213> ORGANISM: Artificial sequence
<220> FEATURE:
<223> OTHER INFORMATION: primer 5'-112-MA-LPCAT-BamHI

<400> SEQUENCE: 12
aggatccatg tcttttacc tcgtcacctt cacc                                  34

<210> SEQ ID NO 13
<211> LENGTH: 27
<212> TYPE: DNA
<213> ORGANISM: Artificial sequence
<220> FEATURE:
<223> OTHER INFORMATION: primer 3'-113-MA-LPCAT_XhoI

<400> SEQUENCE: 13
actcgagtca cgagtacttg acaaggc                                         27

<210> SEQ ID NO 14
<211> LENGTH: 23
<212> TYPE: DNA
<213> ORGANISM: Artificial sequence
<220> FEATURE:
<223> OTHER INFORMATION: primer 5'-118-MA-LPCAT

<400> SEQUENCE: 14
atgtcgaggt cgacggtatc gat                                             23
```

<210> SEQ ID NO 15
<211> LENGTH: 23
<212> TYPE: DNA
<213> ORGANISM: Artificial sequence
<220> FEATURE:
<223> OTHER INFORMATION: primer OtLPCAT-forward

<400> SEQUENCE: 15
accatgctgg tcgcgcgcgt ccg                                   23

<210> SEQ ID NO 16
<211> LENGTH: 20
<212> TYPE: DNA
<213> ORGANISM: Artificial sequence
<220> FEATURE:
<223> OTHER INFORMATION: primer OtLPCAT-reverse

<400> SEQUENCE: 16
tcacgagttg ttcacgaggc                                       20

<210> SEQ ID NO 17
<211> LENGTH: 31
<212> TYPE: DNA
<213> ORGANISM: Artificial sequence
<220> FEATURE:
<223> OTHER INFORMATION: primer PSUN-OtLPCAT-forward

<400> SEQUENCE: 17
gcggccgcac catgctggtc gcgcgcgtcc g                          31

<210> SEQ ID NO 18
<211> LENGTH: 28
<212> TYPE: DNA
<213> ORGANISM: Artificial sequence
<220> FEATURE:
<223> OTHER INFORMATION: primer PSUN-OtLPCAT-reverse

<400> SEQUENCE: 18
gcggccgctc acgagttgtt cacgaggc                              28

<210> SEQ ID NO 19
<211> LENGTH: 60
<212> TYPE: DNA
<213> ORGANISM: Artificial sequence
<220> FEATURE:
<223> OTHER INFORMATION: T7 standard primer

<400> SEQUENCE: 19
gtcgacccgc ggactagtgg gccctctaga cccgggggat ccggatctgc tggctatgaa     60

<210> SEQ ID NO 20
<211> LENGTH: 23
<212> TYPE: DNA
<213> ORGANISM: Artificial sequence
<220> FEATURE:
<223> OTHER INFORMATION: oligonucleotide primer

<400> SEQUENCE: 20
accatgtctt tttacctcgt cac                                   23

<210> SEQ ID NO 21
<211> LENGTH: 20
<212> TYPE: DNA
<213> ORGANISM: Artificial sequence
<220> FEATURE:

-continued

<223> OTHER INFORMATION: oligonucleotide primer

<400> SEQUENCE: 21
tcacgagtac ttgacaaggc                                                    20

<210> SEQ ID NO 22
<211> LENGTH: 23
<212> TYPE: DNA
<213> ORGANISM: Artificial sequence
<220> FEATURE:
<223> OTHER INFORMATION: oligonucleotide primer

<400> SEQUENCE: 22
accatgtcga ggtcgacggt atc                                                23

<210> SEQ ID NO 23
<211> LENGTH: 20
<212> TYPE: DNA
<213> ORGANISM: Artificial sequence
<220> FEATURE:
<223> OTHER INFORMATION: oligonucleotide primer

<400> SEQUENCE: 23
tcacgagtac ttgacaaggc                                                    20

<210> SEQ ID NO 24
<211> LENGTH: 31
<212> TYPE: DNA
<213> ORGANISM: Artificial sequence
<220> FEATURE:
<223> OTHER INFORMATION: primer PSUN-MsLPCAT112-forward

<400> SEQUENCE: 24
gcggccgcac catgtctttt tacctcgtca c                                       31

<210> SEQ ID NO 25
<211> LENGTH: 28
<212> TYPE: DNA
<213> ORGANISM: Artificial sequence
<220> FEATURE:
<223> OTHER INFORMATION: primer PSUN-MsLPCAT112-reverse

<400> SEQUENCE: 25
gcggccgctc acgagtactt gacaaggc                                           28

<210> SEQ ID NO 26
<211> LENGTH: 31
<212> TYPE: DNA
<213> ORGANISM: Artificial sequence
<220> FEATURE:
<223> OTHER INFORMATION: primer PSUN-MsLPCAT118-forward

<400> SEQUENCE: 26
gcggccgcac catgtcgagg tcgacggtat c                                       31

<210> SEQ ID NO 27
<211> LENGTH: 28
<212> TYPE: DNA
<213> ORGANISM: Artificial sequence
<220> FEATURE:

<223> OTHER INFORMATION: primer PSUN-MsLPCAT118-reverse

<400> SEQUENCE: 27
gcggccgctc acgagtactt gacaaggc　　　　　　　　　　　　　　　　28

<210> SEQ ID NO 28
<211> LENGTH: 282
<212> TYPE: PRT
<213> ORGANISM: C. elegans

<400> SEQUENCE: 28

```
Met Glu Asn Phe Trp Ser Ile Val Val Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280
```